(12) United States Patent
Dudar et al.

(10) Patent No.: US 10,943,686 B2
(45) Date of Patent: *Mar. 9, 2021

(54) PATIENT INFORMATION SOFTWARE SYSTEM INCLUDING INFUSION MAP

(71) Applicants: BAXTER INTERNATIONAL INC., Deerfield, IL (US); BAXTER HEALTHCARE S.A., Glattpark (CH)

(72) Inventors: Thomas Edward Dudar, Palatine, IL (US); Steven Clarence Jepson, Vernon Hills, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 151 days.

This patent is subject to a terminal disclaimer.

(21) Appl. No.: 16/221,117

(22) Filed: Dec. 14, 2018

(65) Prior Publication Data

US 2019/0122755 A1    Apr. 25, 2019

Related U.S. Application Data

(63) Continuation of application No. 14/020,483, filed on Sep. 6, 2013, now Pat. No. 10,157,266.

(Continued)

(51) Int. Cl.
G16H 20/17  (2018.01)
G16H 40/63  (2018.01)
G06F 19/00  (2018.01)

(52) U.S. Cl.
CPC ............ *G16H 20/17* (2018.01); *G06F 19/00* (2013.01); *G16H 40/63* (2018.01)

(58) Field of Classification Search
CPC ........ G16H 20/10; G16H 20/17; G16H 40/63; G16H 40/67

(Continued)

(56) References Cited

U.S. PATENT DOCUMENTS 4,526,404 A    7/1985  Vazquez
5,048,870 A    9/1991  Mangini et al.
(Continued)

FOREIGN PATENT DOCUMENTS

CN    102122312 A    7/2011
CN    103077321 A    5/2013
(Continued)

OTHER PUBLICATIONS

Statement in accordance with the Notice from the EP Patent Office dated Oct. 1, 2007, concerning business methods; Nov. 1, 2007.

*Primary Examiner* — Hiep V Nguyen
(74) *Attorney, Agent, or Firm* — Greer, Burns & Crain, Ltd.

(57) ABSTRACT

An infusion map system includes a memory storing at least infusion mapping instructions, and a processor that executes the stored instructions. When the processor executes the infusion mapping instructions, the infusion map system performs a displaying function that displays at least a portion of an electronic medical record associated with a patient and a diagramming function that receives the electronic medical record and generates an infusion map showing all intravenous drugs being administered to the patient. For each of the drugs, the infusion map further illustrates a route of administration for the drug. An order administering function performed by the system allows a user to alter the infusion map, and a record updating function of annotating the electronic medical record to correspond to the altered infusion map.

14 Claims, 46 Drawing Sheets

Related U.S. Application Data

(60) Provisional application No. 61/697,648, filed on Sep. 6, 2012.

(58) Field of Classification Search
USPC .............................................................. 705/3
See application file for complete search history.

(56) References Cited

U.S. PATENT DOCUMENTS

| | | | |
|---|---|---|---|
| 5,090,779 A | 2/1992 | Kramer | |
| 5,180,287 A | 1/1993 | Natwick et al. | |
| 5,329,927 A | 7/1994 | Gardineer et al. | |
| 5,782,495 A | 7/1998 | Grosskopf et al. | |
| 5,799,981 A | 9/1998 | Tung et al. | |
| 5,855,395 A | 1/1999 | Foote et al. | |
| 5,958,536 A | 9/1999 | Gelsinger et al. | |
| 5,974,708 A | 11/1999 | Webb et al. | |
| 6,035,568 A | 3/2000 | Grosskopf et al. | |
| 6,142,008 A | 11/2000 | Cole et al. | |
| 6,410,111 B1 | 6/2002 | Roth et al. | |
| 6,468,242 B1 | 10/2002 | Wilson et al. | |
| 6,988,075 B1 | 1/2006 | Hacker | |
| 7,092,797 B2 | 8/2006 | Gaines et al. | |
| 7,455,662 B2 | 11/2008 | Kraushaar | |
| 8,266,878 B2 | 9/2012 | Luciano, Jr. et al. | |
| 8,317,770 B2 | 11/2012 | Miesel et al. | |
| 8,571,881 B2 | 10/2013 | Rousso et al. | |
| 8,597,271 B2 | 12/2013 | Langan et al. | |
| 8,808,249 B2 | 8/2014 | Langan et al. | |
| 8,965,707 B2 * | 2/2015 | Blomquist | G06F 19/3468 |
| | | | 702/19 |
| 2002/0038392 A1 | 3/2002 | De La Huerga | |
| 2002/0056989 A1 | 5/2002 | Lewis-Leander | |
| 2002/0077852 A1 | 6/2002 | Ford et al. | |
| 2006/0081255 A1 | 4/2006 | Miller et al. | |
| 2006/0265246 A1 | 11/2006 | Hoag | |
| 2007/0016450 A1 | 1/2007 | Bhora et al. | |
| 2007/0088286 A1 | 4/2007 | Brier | |
| 2007/0107517 A1 | 5/2007 | Arnold | |
| 2007/0208595 A1 | 9/2007 | Ohmura et al. | |
| 2007/0233520 A1 | 10/2007 | Wehba et al. | |
| 2008/0046288 A1 | 2/2008 | Menon et al. | |
| 2008/0126969 A1 | 5/2008 | Blomquist | |
| 2009/0053071 A1 | 2/2009 | Wang et al. | |
| 2010/0094653 A1 | 4/2010 | Tribble et al. | |
| 2010/0152644 A1 * | 6/2010 | Pesach | A61M 5/16831 |
| | | | 604/20 |
| 2011/0071844 A1 * | 3/2011 | Cannon | G06F 19/3468 |
| | | | 705/2 |
| 2013/0289496 A1 | 10/2013 | Langan et al. | |
| 2014/0130909 A1 | 5/2014 | Dudar et al. | |
| 2014/0262252 A1 | 9/2014 | Slepicka et al. | |
| 2014/0326629 A1 | 11/2014 | Langan et al. | |

FOREIGN PATENT DOCUMENTS

| | | |
|---|---|---|
| JP | 109218887 A | 8/1997 |
| JP | 2001333979 A | 12/2001 |
| JP | 2003271732 A | 9/2003 |
| JP | 2005284855 A | 10/2005 |
| JP | 2006092247 A | 4/2006 |
| JP | 2006309300 A | 11/2006 |
| JP | 2009273502 A | 11/2009 |
| JP | 2011048443 A | 3/2011 |
| WO | 2003/098534 A1 | 11/2003 |
| WO | 2014/055434 A1 | 4/2014 |

* cited by examiner

Fig.10

Tablet

00:00 PM

Patient List

Infusion Status - John Doe — 30

Logged in as Susan Edwards, RN (ok) John Doe
(ok) Patrick Fitz
(ok) Elaine Johnson
(ok) Wendy Jones

26

PATIENT INFORMATION

NAME: John Doe
DATE OF BIRTH: 10/12/1982
ID NUMBER: 4323563
ROOM: 511

View Infusion Map

HISTORY — 34

36

| | | |
|---|---|---|
| Today 12:34 pm | STARTED | Replace Insulin 100 units/100mL (1unit/mL) |
| Yesterday 10:03 pm | STARTED | Lactated Ringers |
| Yesterday 9:45 pm | STARTED | Phenylephrine 40 mg/250 mL (0.16 mg/mL) |
| Yesterday 5:46 pm | STARTED | DOPamine 400 mg/250 mL (1.6 mg/mL) |
| Yesterday 5:40 pm | PLACED | PICC Catheter |

Training and Instructions for Use

Scenarios

| Tablet 📶 | | 00:00 PM | | | | Logged in as Susan Edwards, RN |
|---|---|---|---|---|---|---|

Patient List

Infusion Status - John Doe

—30

John Doe (OK)

PATIENT INFORMATION

Patrick Fitz (OK)

| NAME | ID NUMBER: |
|---|---|
| John Doe | 4323563 |
| DATE OF BIRTH: | ROOM: |
| 10/12/1982 | 511 |

Elaine Johnson (OK)

Wendy Jones (OK)

View Infusion Map

Robert Smith ●

HISTORY ⌒34

28⤴ ⤶26

| Yesterday 9:45 pm | DICONTINUED | Vancomycin 1g/250 mL |  |
|---|---|---|---|
| Today 12:35 pm | STARTED | Heparin 25000 units/250 mL (100 units/mL) | 36— |
| Today 12:34 pm | STARTED | Replace Insulin 100 units/100mL (1unit/mL) | |
| Yesterday 10:03 pm | STARTED | Lactated Ringers | |
| Yesterday 9:45 pm | STARTED | Phenylephrine 40 mg/250 mL (0.16 mg/mL) | |
| Yesterday 5:46 pm | STARTED | DOPamine 400 mg/250 mL (1.6 mg/mL) | |
| Yesterday 5:40 pm | PLACED | PICC Catheter | |

Training and Instructions for Use | Scenarios

Fig.30

Patient List

Tablet

00:00 PM

| Patient List | Infusion Status - Robert Smith | Logged in as Susan Edwards, RN |

- (OK) John Doe
- (OK) Patrick Fitz
- (OK) Elaine Johnson
- (OK) Wendy Jones
- ● Robert Smith ← 26

PATIENT INFORMATION — 30

NAME: Robert Smith
ID NUMBER: 4323578
DATE OF BIRTH: 7/2/1943
ROOM: 515

View Infusion Map

ACTIONS — 28
- Today 12:39 pm    NEW ORDER — 32    Insulin 100 units/100 mL (1 unit/mL) — 36

HISTORY — 34
- Today 12:05 pm    NEW PATIENT    Patient admitted to floor

Training and Instructions for Use

Scenarios

Patient List

- OK John Doe
- OK Patrick Fitz
- OK Elaine Johnson
- OK Wendy Jones
- OK Robert Smith  — 26

Infusion Status - Robert Smith — 30

Logged in as Susan Edwards, RN

00:00 PM

PATIENT INFORMATION

NAME: Robert Smith
DATE OF BIRTH: 7/2/1943
ID NUMBER: 4323578
ROOM: 515

View Infusion Map

HISTORY — 34

| Today 12:42 pm | STARTED | Insulin 100 untis/100 mL (1 unit/mL) | — 36 |
| Today 12:05 pm | NEW PATIENT | Patient admitted to floor |

Scenarios

Training and Instructions for Use

PATIENT INFORMATION SOFTWARE SYSTEM INCLUDING INFUSION MAP

RELATED APPLICATIONS

The present application is a Continuation application of U.S. patent application Ser. No. 14/020,483 filed Sep. 6, 2013, which claims 35 USC 119 priority from U.S. Patent Application Ser. No. 61/697,648, filed Sep. 6, 2012, which is incorporated by reference.

FIELD OF THE INVENTION

This invention relates to patient information software, and more particularly to software for displaying a patient-specific, interactive, real-time infusion system map.

BACKGROUND

Currently, medication delivery systems are limited due to the number of parties involved in medicating a hospitalized patient, and a lack of complete, consistent information provided to all parties. Typically, physicians write prescriptions for patients. Pharmacists fill and dispense the prescriptions without knowledge of the patient's infusion setup (route of administration of the various drugs prescribed is often unspecified or underspecified). Nurses are responsible for administering the prescribed drugs according to instructions from both the physicians and pharmacists. This leads to nurses making critical decisions about infusion setup and drug administration, which can lead to errors. In particular, the above workflow can, among other things, lead to unnoticed drug incompatibilities, inadvertent bolus, excessive lag time, and errors in the "five rights" of drug administration (ensuring the right patient, right drug, right dose, right time, and right administration route).

Pharmacists lack the ability to see the physical infusion system as created by the administering nurses. Accordingly, the pharmacists rely on the patient's medical record when checking and filling prescriptions. Nurses manually map, label, and trace the various infusion lines. The nurse also manually selects a route, port, and catheter hub for a newly-added drug deliverable by infusion, and manually records this information in the patient's medical administration record (MAR). Typically, a single nurse is responsible for many patients throughout a shift, and is constantly receiving, discharging, and transferring patients. Accordingly, medical records may lack the specificity required for a pharmacist to fully verify that there are no undesired drug interactions.

Accordingly, there is a need to provide a system for health care professionals to view an accurate representation of a patient's infusion map in real time. Likewise, there is a need to provide a system that aids clinicians in accurately recording the patient's infusion map in his or her medical record. Likewise, there is a need to provide a system that models infusion setups to aid decision making and execution by clinicians to reduce medication errors and save time.

SUMMARY

A patient information software system with infusion map addresses these needs. The system provides an accurate and up-to-date representation of each patient's infusion map, and allows clinicians to easily modify the presented map. The system further updates the patient's electronic medical record to reflect changes made to the infusion map, thus assisting the clinicians with their record-keeping requirements. Further, the present system aids clinicians in verifying the infusion setup before administering a drug to a patient, thus helping to reduce errors and save time.

In a first aspect, a patient information software system includes a memory storing at least infusion mapping instructions, and a processor that executes the stored instructions. When the processor executes the infusion mapping instructions, the infusion map system performs a displaying function that displays at least a portion of an electronic medical record associated with a patient, and a diagramming function that receives the electronic medical record and generates an infusion map showing all intravenous drugs being administered to the patient. For each of the drugs, the infusion map further illustrates a route of administration for the drug. An order administering function performed by the system allows a user to alter the infusion map, and a record updating function of annotating the electronic medical record to correspond to the altered infusion map.

In another aspect, an infusion mapping process includes retrieving and displaying at least a portion of an electronic medical record associated with a patient, and generating an infusion map schematically showing all intravenous drugs being administered to the patient based on the retrieved electronic medical record. For each of the drugs, the schematic diagram illustrates a route of administration for the drug. The process further includes receiving a new order that alters the infusion map, and updating the electronic medical record to correspond to the altered infusion map.

In still another aspect, a hospital information system includes an electronic medical record server maintaining a plurality of patient electronic medical records, and an infusion mapping device in communication with the electronic medical record server. The infusion mapping device performs operations including retrieving at least a portion of one or more of the plurality of patient electronic medical records, including a portion specifying intravenous drugs being administered to the patient and hospital equipment associated with the administration of the drugs. For each of the one or more retrieved medical records, the infusion mapping device displays an infusion map that schematically represents the portion of the medical record specifying intravenous drugs being administered and associated hospital equipment. The device modifies the infusion map and updates the electronic medical record based on the modified infusion map. Finally, the device saves the updated electronic medical record to the electronic medical record server.

BRIEF DESCRIPTION OF THE DRAWINGS

FIGS. 2-46 show example screenshots of the patient information software system with infusion map of FIG. 1.

DETAILED DESCRIPTION

Figure 1:
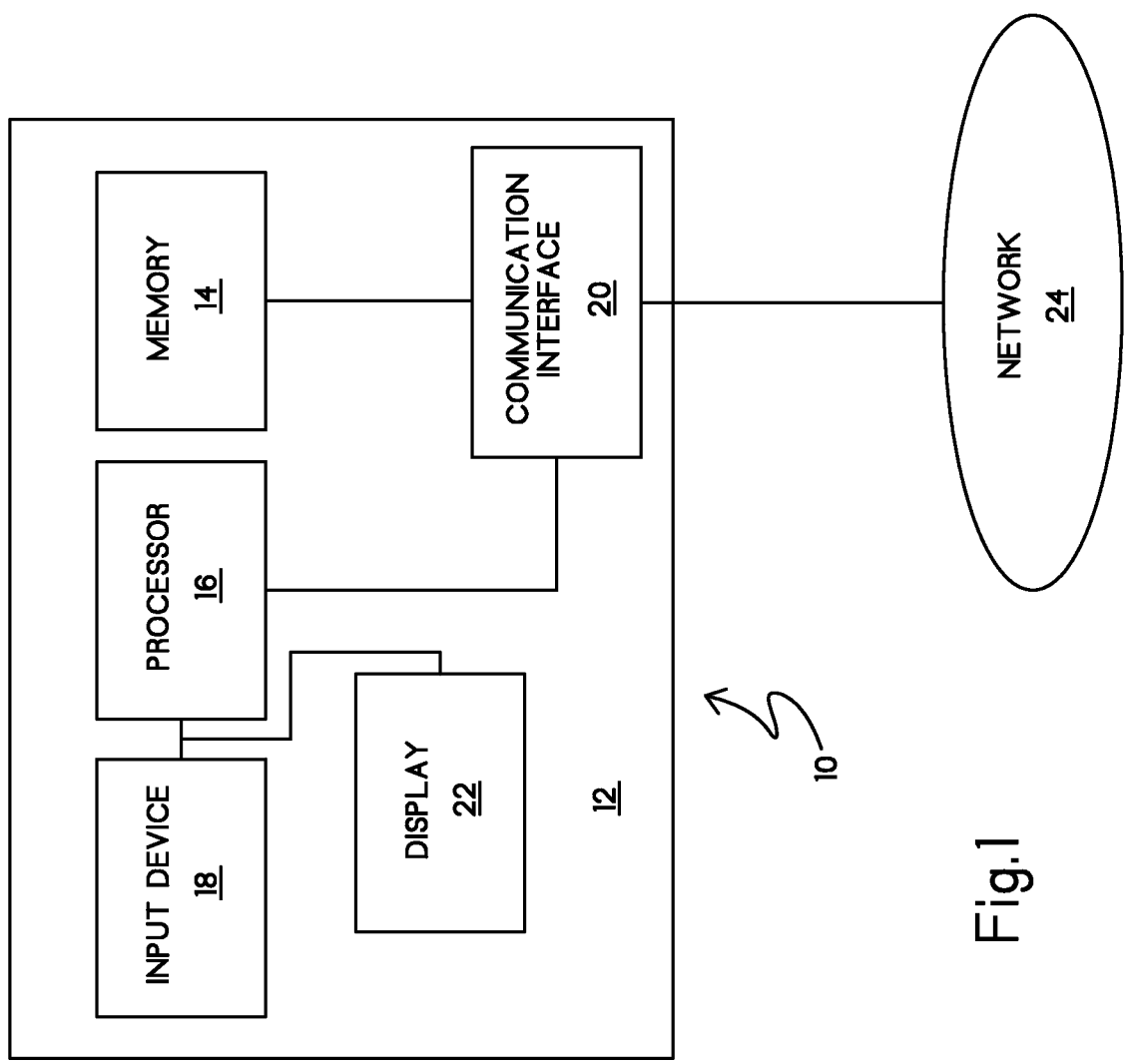
FIG. 1 is a schematic diagram of a patient information software system with infusion map.

A patient information software system with infusion map is generally designated 10. The system 10 includes a computerized device 12, having at least a memory 14, a processor 16, an input device 18, a network communication interface 20, a display 22, and a power source (not shown). The memory 14 is preferably a non-transitory computer-readable recording medium, such as a read only memory (ROM), random access memory (RAM), hard disk, non-volatile flash memory or other electronically erasable programmable read-only memories (EEPROMs), or optical or magneto-optical memory storage medium. The memory 14 stores instructions that, when executed, perform the infusion mapping. The computerized device 12 also includes the processor 16, which may be, for example, a microprocessor or other central processing unit capable of executing the instructions stored in the memory 14. The display 22 is a device such as a liquid crystal display, cathode ray tube, plasma display, or other device capable of outputting data from the memory 14 and processor 16 in a way that is easily discernible by a user.

The network communication interface 20 allows the device 12 to connect to a network 24, such as a local area network (LAN), wide area network (WAN), and/or the Internet. The interface 20 connects to the network 24 via a wired connection using, for example, the Institute of Electrical and Electronics Engineers (IEEE) 802.3 standard, or a wireless connection using standards such as IEEE 802.11a/b/g/n/ac, or any newly developed standards that supersede these. The network interface 20 may also connect to one or more cellular data networks using standards such and protocols as Long Term Evolution (LTE), Worldwide Interoperability for Microwave Access (WiMAX), Global System for Mobile Communications (GSM), Code Division Multiple Access (CDMA) standards such as cdmaOne and CDMA2000, High Speed Packet Access (HSPA), Evolved HSPA (HSPA+), General Packet Radio Services (GPRS), and the like.

The computerized device 12 may take many forms, including a laptop or desktop computer, a client computer integrated with a hospital information system to allow for access at multiple locations (e.g., pharmacy, nursing station, emergency department, diagnostic laboratory, and physician offices), a portable device such as a tablet, smartphone, personal digital assistant, or computer on wheels. Additionally, the computerized device may be integrated into bedside equipment such as infusion pumps and/or patient monitors.

The memory 14 on the system 10 stores a patient list that includes a plurality of records listing each current patient, together with patient ID information (ID number, date of birth, room number within the hospital, etc.), an infusion map, a list of pending activities related to the patient's infusion system, a list of past activities related to the infusion system, and optionally a list of personnel authorized to view the patient's record. The patient list is preferably maintained in a central storage location accessible by all users of the infusion mapping system.

Each infusion map stores a list of drugs prescribed and/or being administered intravenously to a patient. One convenient method to maintain this information is to integrate the system with the institution's Computerized Prescription Order Entry (CPOE) system, or other similar institution system, typically centralized in the hospital pharmacy. Preferably each drug is stored in combination with at least a dosage (concentration) of the drug, a volume of liquid in which the drug is diffused, a rate at which the fluid is being administered to the patient, a specific pump (if any) used to facilitate the administration, a catheter port at which the drug is entering the patient's bloodstream, and an indication of what tubing connects the drug container to the catheter. One of skill in the art will recognize that more or different information may be stored as part of the infusion map without departing from the scope of this invention.

When a user interacts with the system 10 through a computerized device, he will be provided with a login prompt, requiring that the user provide authentication credentials for the system. Such credentials may include, but are not limited to a unique username, password, and/or biometric identification such as a fingerprint, voice sample, facial image or the like. The system 10 will verify the provided login credentials and once the system has verified the user, the system displays a user name on screen so that the user can easily verify that he or she is logged in correctly, and can easily distinguish his or her device from other similar devices. The system 10 also uses this username when documenting data input and actions taken.

Figure 2:
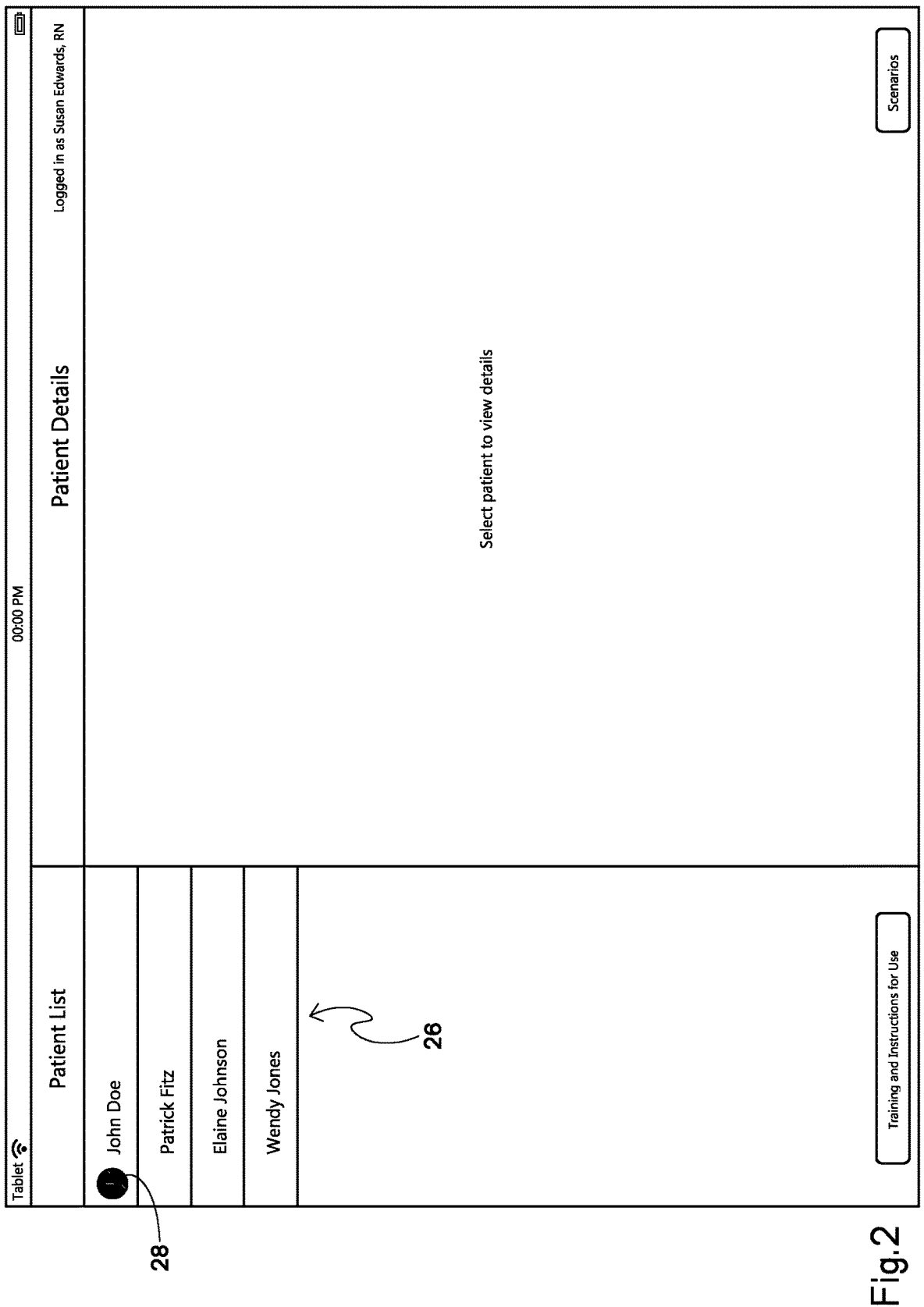

Once the user logs into the system 10, the system presents a patient list 26, as shown in FIG. 2. Alternatively, the user may be presented with a triage list of required actions corresponding to the patient workload in place of or in addition to the patient list. To present the patient list 26, the system 10 retrieves a list of patient names from the patient table, and displays a list of current patients, as shown in FIG. 2. If the patient table restricts access of the patient records to particular users, the system compares the user ID of the logged-in user to the list or personnel authorized to view the patient record stored in the patient table, and displays only those patient names corresponding to records the logged-in user is authorized to view. Additionally, the patient list 26 preferably includes a notification icon 28 indicating that some action is required for a patient. In the example shown in FIG. 2, the exclamation point icon indicates that there is an action required for patient "John Doe."

Figure 3:
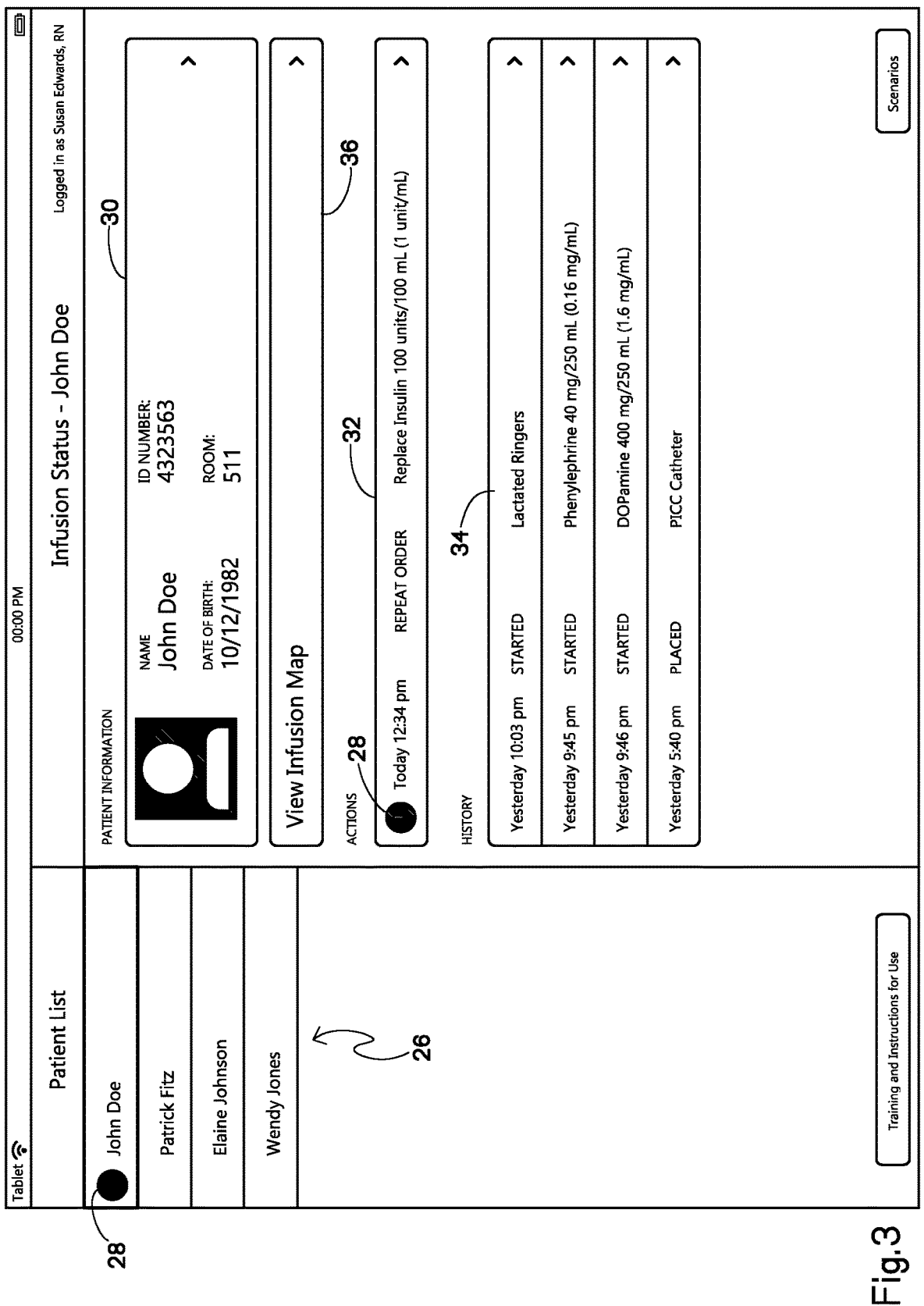

The user then selects a patient from among the list of patients displayed. For example, the user may select "John Doe" from the patient list 26. As shown in FIG. 3, when a patient is selected, infusion status of the selected patient is retrieved from the patient table and displayed to the user in an easily-readable manner. The displayed infusion status includes patient identification information 30, a list of all pending actions required for the patient 32, a list of all actions previously recorded for that patient 34, and a link 36 to view the infusion map associated with the patient.

Figure 4:
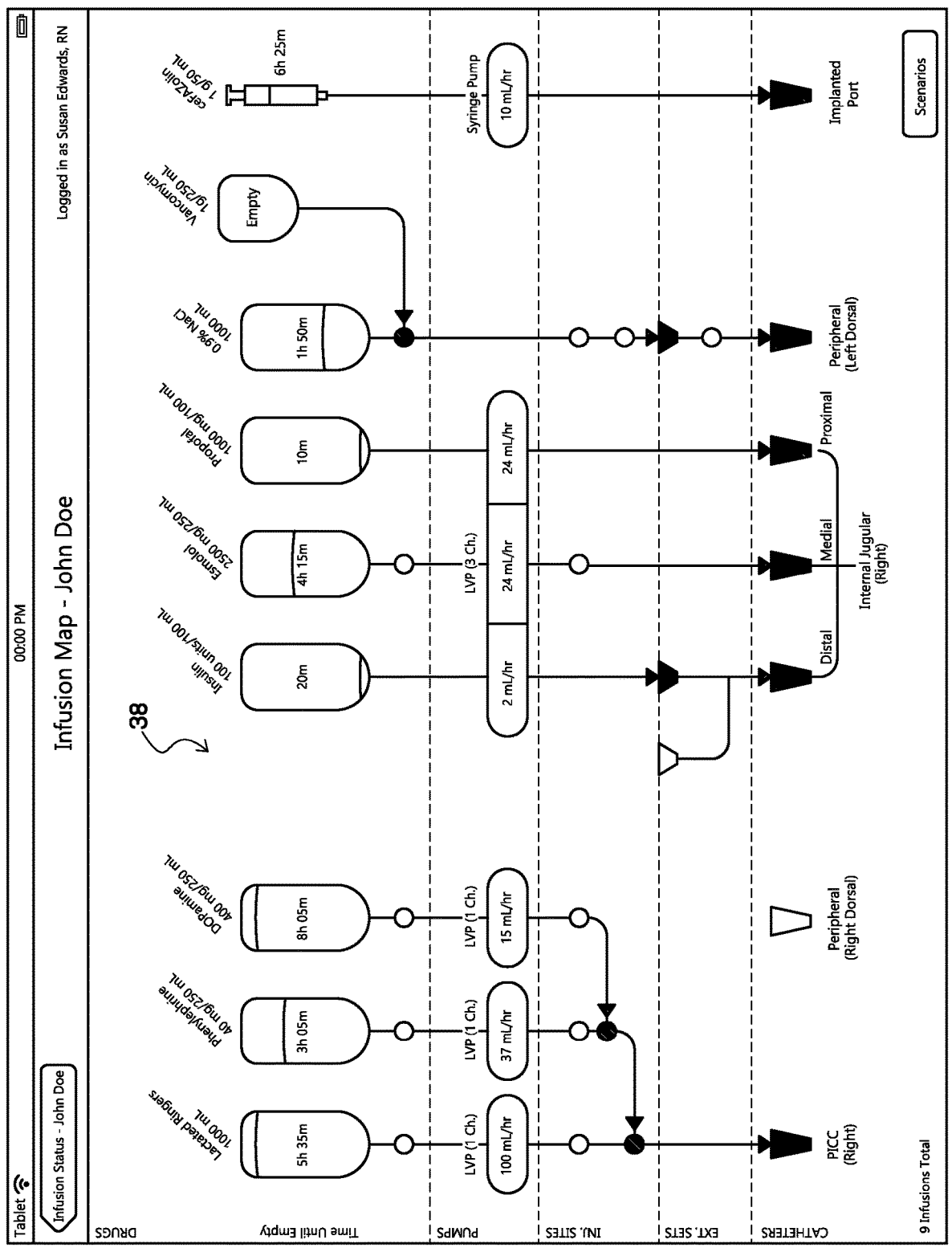

As shown in FIG. 4, when user selects the link 36 to the patient infusion map, the system retrieves the stored infusion map and builds a graphical representation of the map 38, which schematically illustrates the various drugs currently being administered intravenously to the patient, to display to the user. The infusion map 38 preferably shows each of the infusion drugs connected to the patient, together with a graphical representation of several pieces of information related to each drug. In particular, each drug is typically labeled with its name, concentration, volume, and/or amount; a remaining time until that drug is completely infused; a label indicating the specific pump providing the infusion (if any); the rate at which the pump is set; and the site on the patient body to which the drug is connected. As an example, FIG. 4 shows that John Doe is receiving Phenylephrine, in the amount of 40 mg/250 ml; the remaining time before the Phenylephrine is completely infused is 3 hours and 5 minutes; the drug is being infused by a single-channel large volume infusion pump set to a rate of 37 ml per hour, and is connected to a peripherally inserted central catheter (PICC) on the patient's right side. As can be seen in FIG. 4, each drug is similarly labeled.

Figure 5:
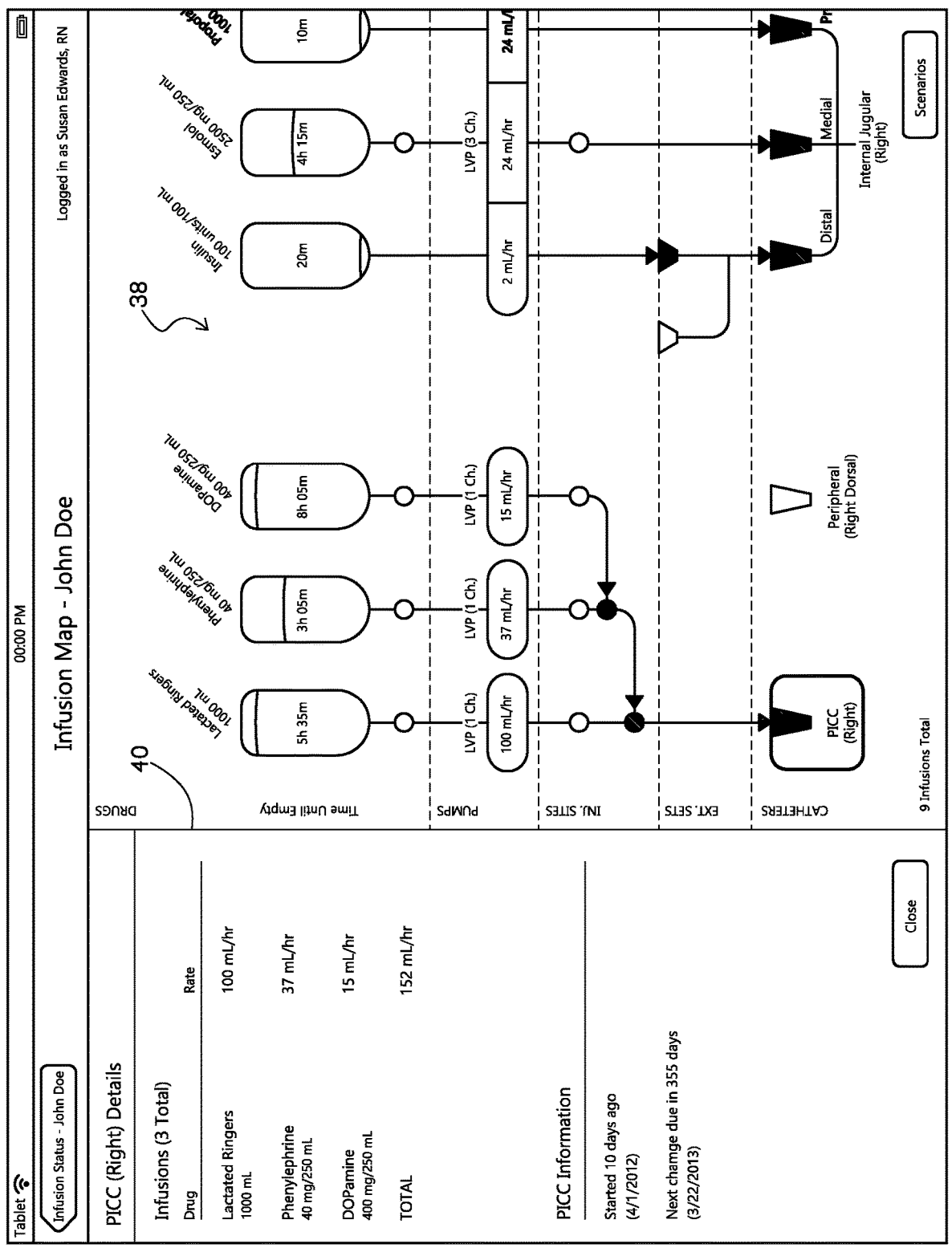

The system 10 stores and can display additional information regarding each of the elements shown on the infusion map. For example, when the PICC is selected, additional information 40 related to that site is displayed, as shown in FIG. 5. The displayed information includes a list of drugs that are connected to the catheter, an infusion rate for each of the drugs, and a total infusion rate for the catheter. The information also includes data relating to when the catheter was inserted and when the catheter should be changed according to best-practice guidelines or any guidelines specified by the hospital. Closing the additional information panel returns the user to the infusion map display.

Figure 6:
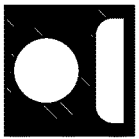
Figure 7:
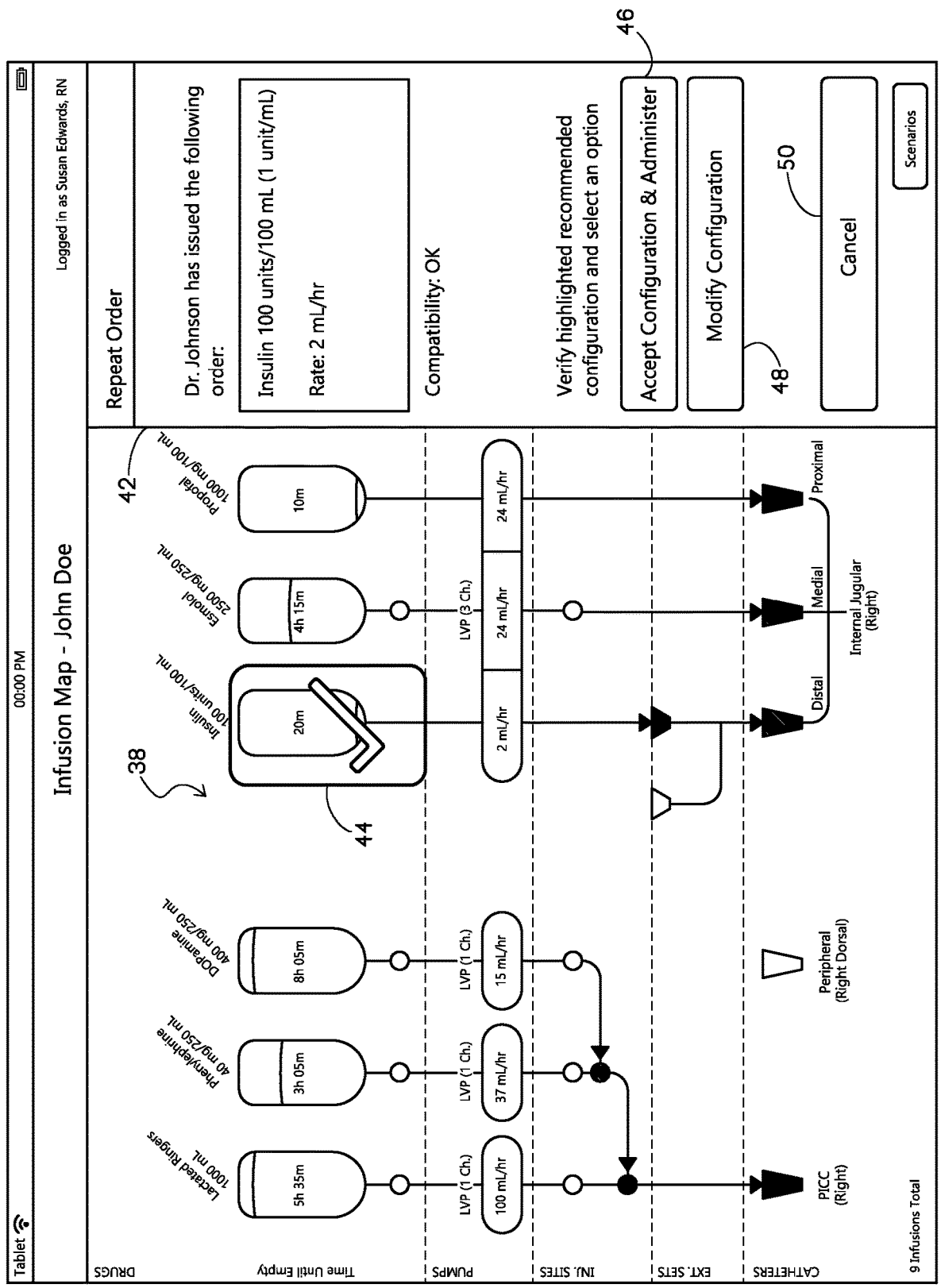

FIGS. 6-10 illustrate one of the various medication delivery workflows the system is capable of facilitating. As shown in FIG. 6, the patient has a pending action item in list 32, indicating that the physician and/or pharmacist has repeated an order for that patient. When a user selects a pending action to repeat an order, the system displays at least a portion of the patient infusion map 38 containing the drug specified in the order, as shown in FIG. 7. Additionally, order information 42 related to the repeat order is shown. The information 42 preferably includes an issuing physician, administration information including amount of drug, amount of fluid, and infusion rate, and compatibility information indicating whether or not the order is compatible with the existing infusion map. Those skilled in the art will recognize that different and/or additional information may be provided without departing from the scope of this invention.

To provide the compatibility information, the system 10 performs a drug compatibility check regarding at least four aspects of drug compatibility. First, the system 10 checks to determine compatibility between the drug and the patient. Specifically, the system determines if the patient has any allergies noted in his medical record that would be relevant to the drug to be administered. Additionally, the system 10 checks for any physical incompatibilities (e.g., precipitation interactions) between drugs prescribed to the patient. Finally, the system 10 includes a mass flow balance model to check for errors in the flow of the drugs into the patient's system. Mass flow balance errors are generally caused by an incorrect placement of a drug within a patient's infusion system, an unexpected or overlooked interaction between multiple infusion pumps, or other issues with the physical equipment used to administer the drugs. Such errors include, for example, an inadvertent bolus (an unintended increase in flow rate, causing a sudden increase in the drug concentration in a patient's blood stream) or an inadvertent lag (unintended delay in administration or decreased flow rate of a drug). The results of this compatibility check make up the compatibility information provided to the user.

The system 10 also highlights 44 a recommended configuration for the order. Recommendations may be made by, for example, the issuing physician or a pharmacist. As shown in FIG. 7, the system 10 suggests replacing the existing insulin infusion bag with a new bag. The system 10 then prompts the user to either accept the suggested configuration and administer the drug 46, modify the suggested configuration 48, or cancel 50. In response to user indication that the configuration is accepted 46, the system then prompts the user to confirm that the order has been administered 52, as shown in FIG. 8.

Figure 8:
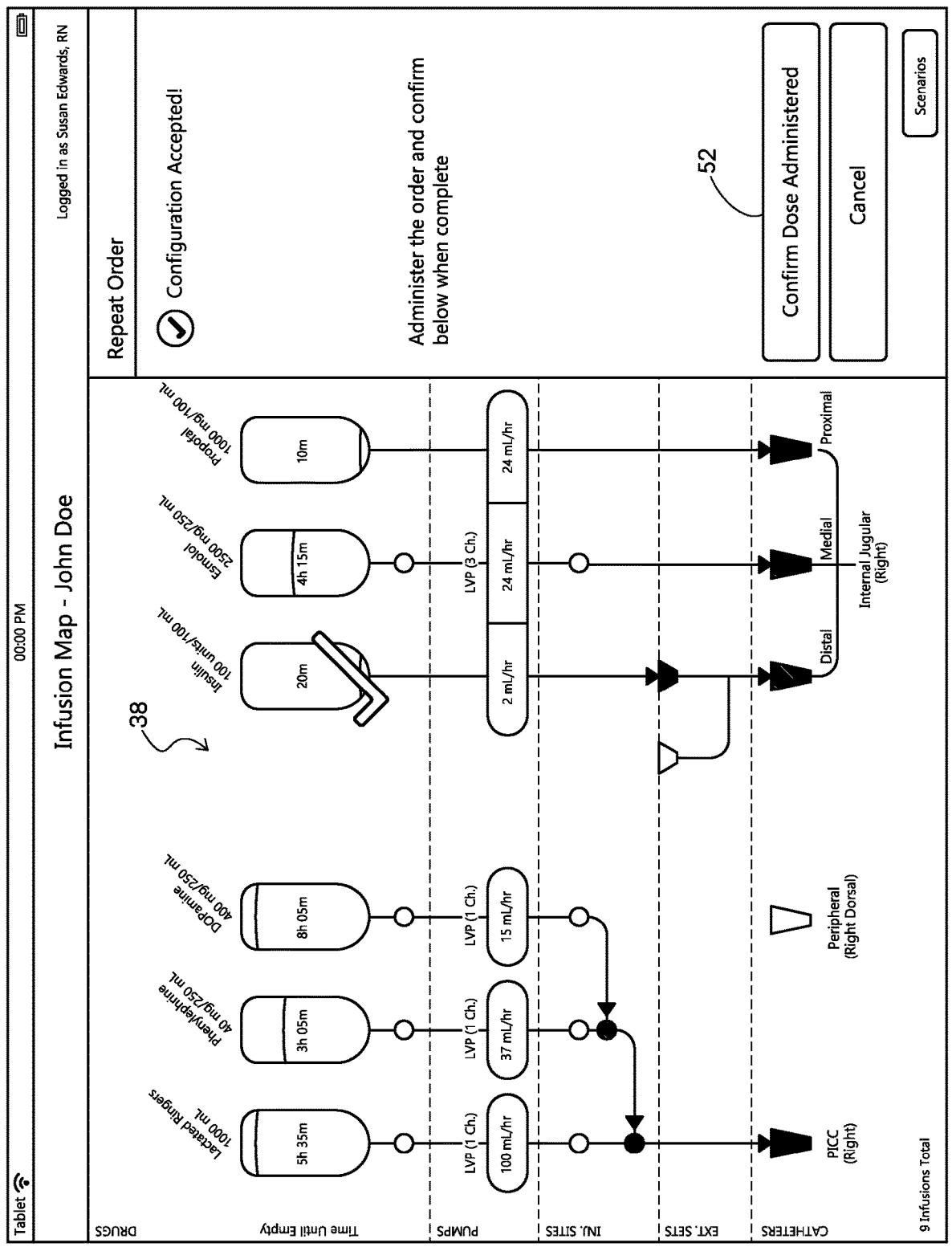
Figure 9:

User confirmation preferably includes a simple click of a confirmation button 52 presented to the user, as shown in FIG. 8. Alternatively, or in addition to this confirmation, the user may be required confirm the dosage administration in other ways. For example, the user may be required to scan a barcode corresponding to the administered drug. This helps to provide additional verification that the order was administered correctly. Once the user indicates that the order was successfully administered, the system 10 displays a confirmation dialog box 54 indicating that the repeat order was successfully administered, as shown in FIG. 9. Additionally, as noted in the confirmation dialog box 54 shown in FIG. 9, when an action is successfully administered, the system 10 automatically annotates the patient's electronic medical record indicating the time the order was administered and the user who administered the order. Once the user clicks OK as shown in FIG. 9, the system 10 returns to the patient infusion status screen as shown in FIG. 10. The screen shows the updated patient history 34 and removes the pending action item.

Figure 11:
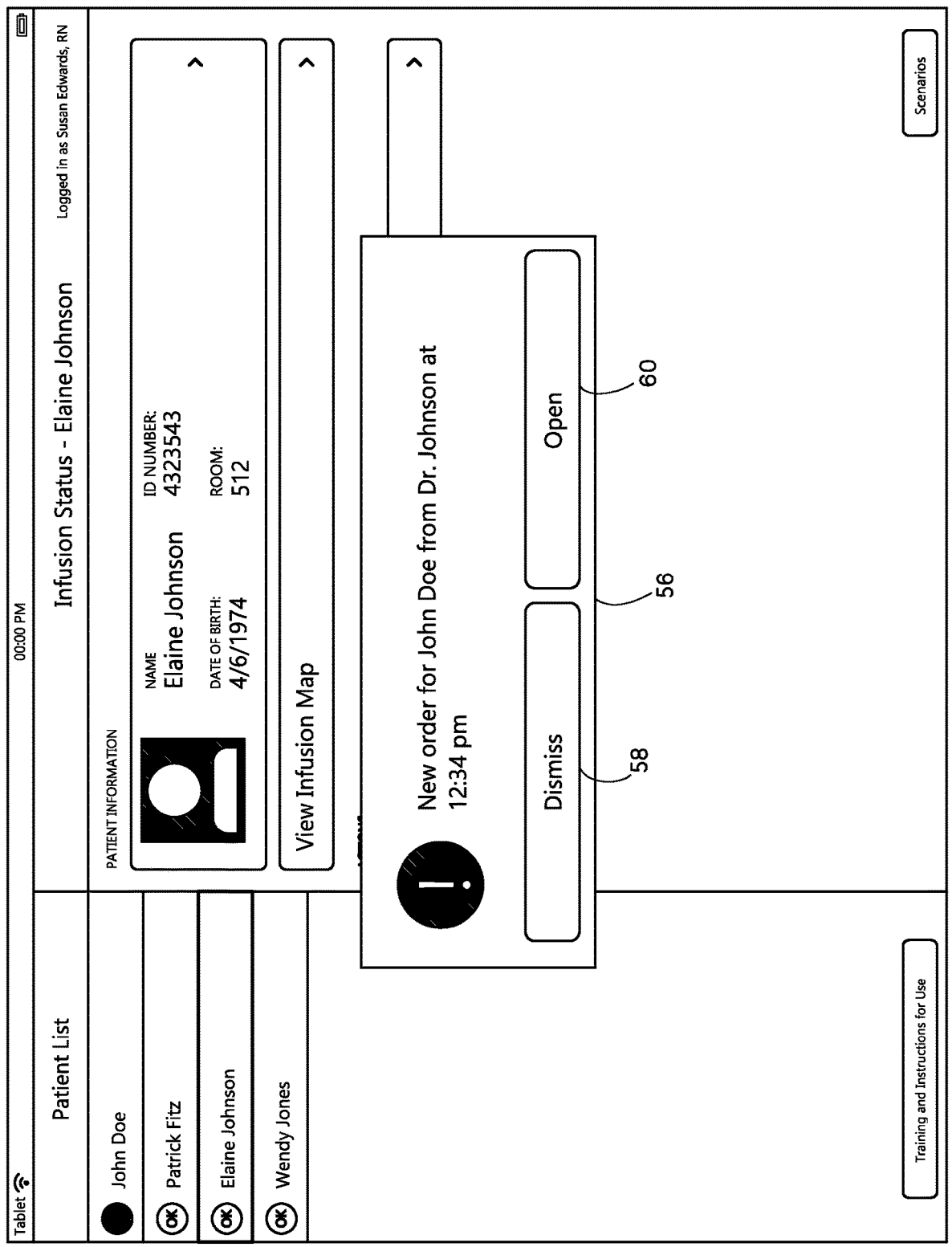

The system 10 also allows for handing of new orders, as shown in FIGS. 11-15. Preferably, the infusion system provides real-time updates regarding incoming orders for a patient under the user's supervision. As shown in FIG. 11, when a new order is received for patient John Doe, a notification 56 is displayed to the user. The user is provided with options to dismiss 58 the notification or to open 60 the patient profile for John Doe.

Figure 12:
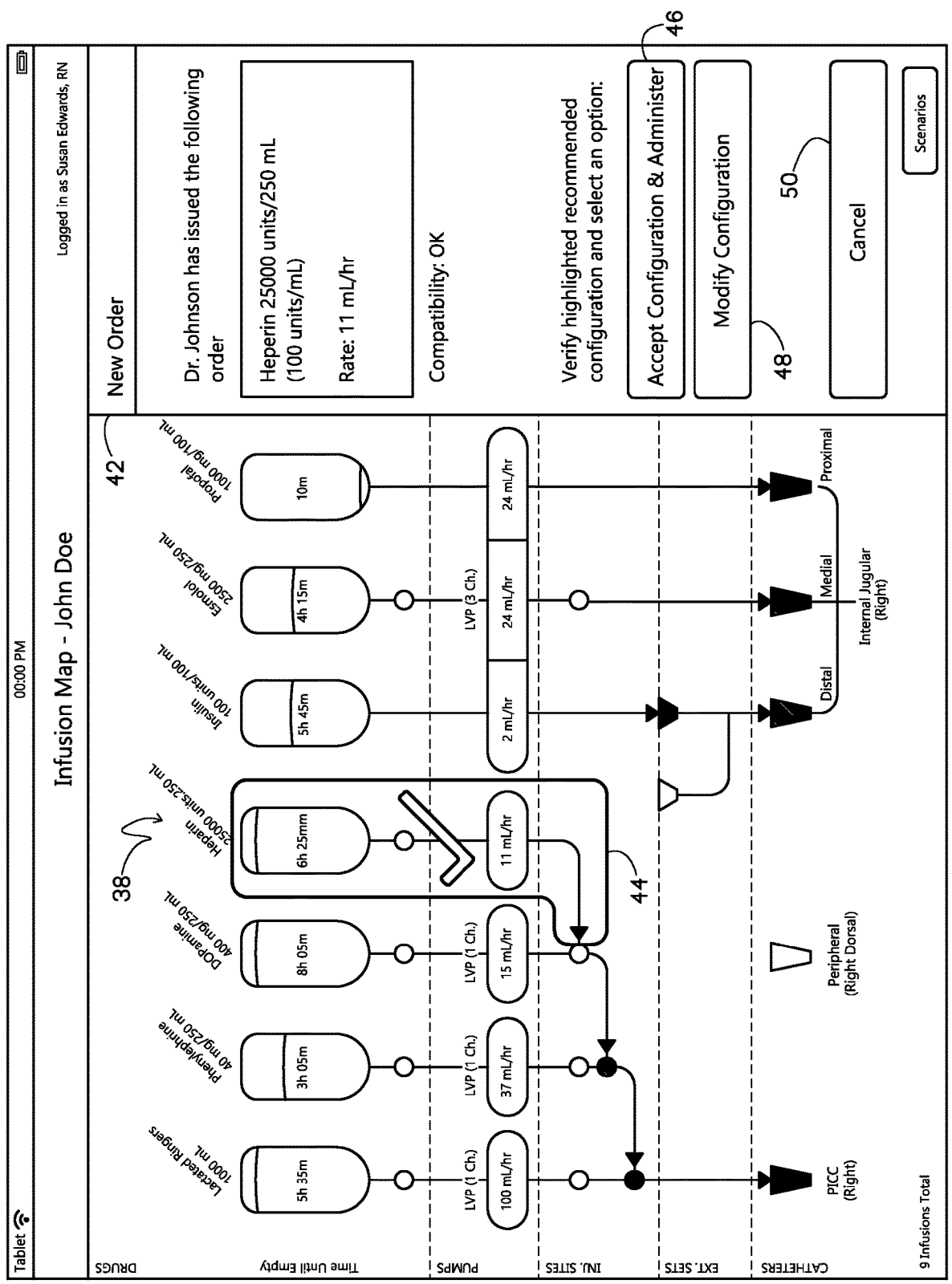
Figure 13:
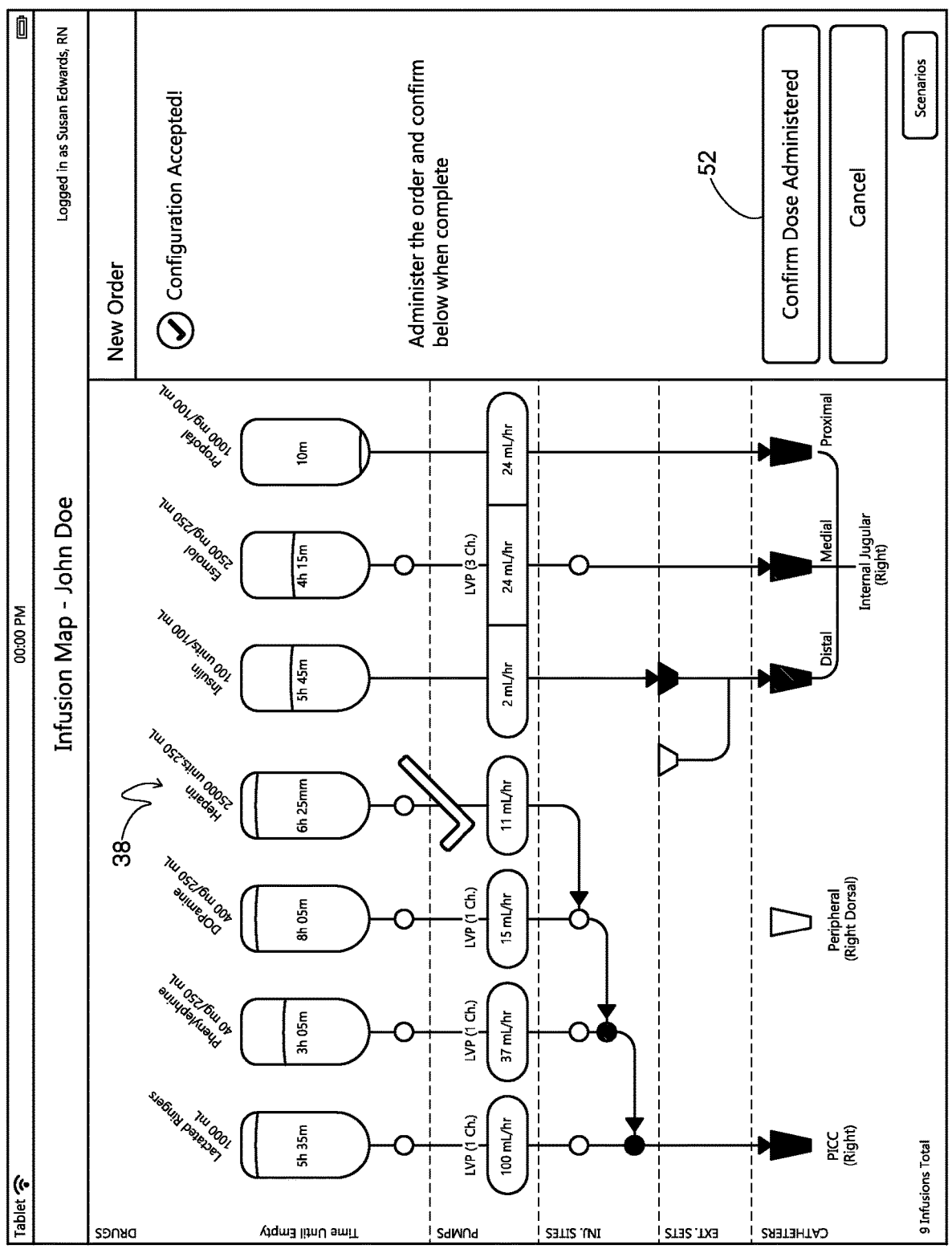
Figure 14:
Figure 15:
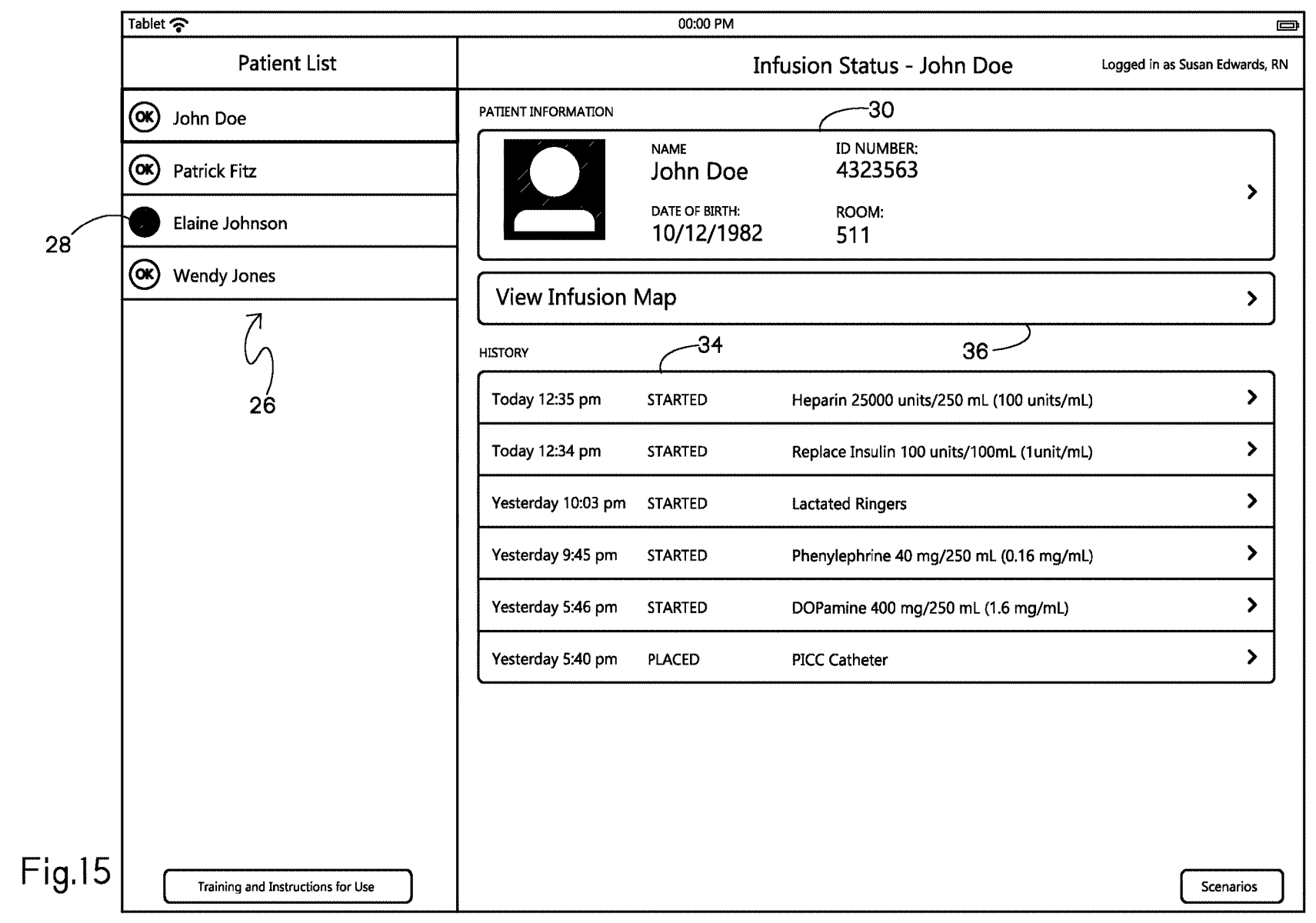

When the user selects "Open" 60 from the new order notification, the system preferably opens the order. FIG. 12 shows the new order screen. As discussed above, the screen includes order information 42 regarding the physician who issued the order, the ordered drug (e.g., number of units of the ordered drug, volume of liquid to be infused, and infusion rate), and compatibility check information indicating that the drug as ordered is compatible with the existing patient infusion map. The system 10 also displays at least a portion of the patient infusion map 38, and a highlighted recommended configuration 44 for administration of the ordered drug. Again, the user is presented with options to accept the suggested configuration and administer the ordered drug 46, modify the configuration 48, or cancel 50. When the user accepts the configuration 46, the infusion map 38 is updated to include the recommended configuration as shown in FIG. 13. The system then prompts the user to confirm that the order has been administered 52. The user then receives a notification dialog box 54 indicating that the dose has been successfully administered, as shown in FIG. 14. The system 10 also updates the patient's electronic medical record to indicate the time at which the order was administered and the user that administered the order, as indicated by the notification dialog box 54 present in FIG. 14. FIG. 15 shows the updated infusion status screen for patient John Doe, reflecting the updated history 34 in the patient's electronic medical record.

Figure 16:

As shown in FIGS. 16-25, the system 10 also allows for additional configuration options when a new order is received. When the user selects another patient from the user list, the infusion status screen corresponding to the patient is displayed, as shown in FIG. 16. The infusion status screen lists a pending action 32 for a new order. When the user selects the pending action 32, the system displays a screen showing the infusion map and the new order information.

Figure 17:
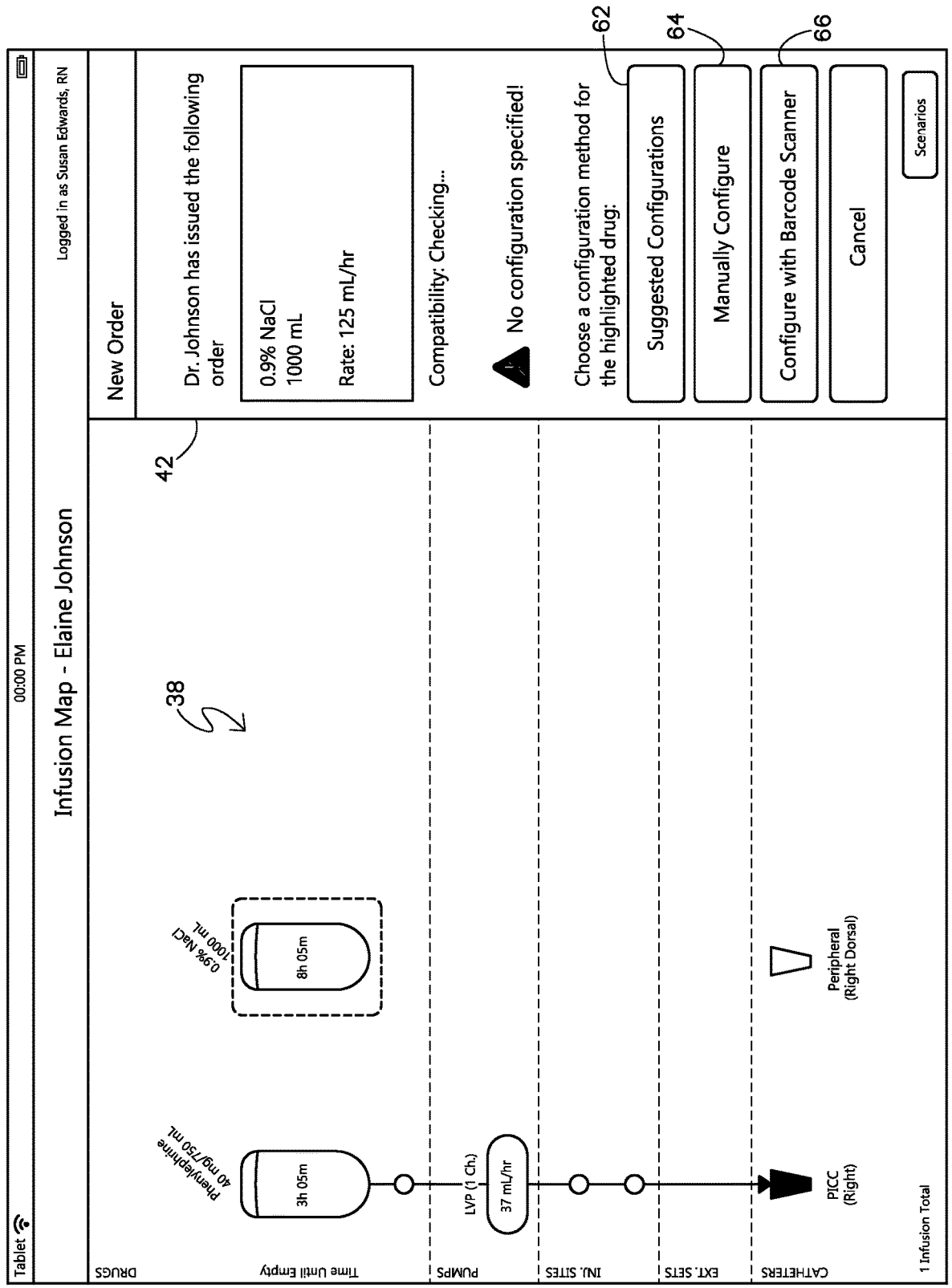

As shown in FIG. 17, the new order information 42 includes information regarding the physician issuing the order, the drug to be administered, the volume of fluid to be infused, and the infusion rate. However, no configuration has been suggested by the physician or pharmacist for administration of the drug. Accordingly, the user is presented with options to retrieve configurations suggested by the system 62, manually configure the infusion 64, or to configure the drug infusion using a barcode scanner 66.

The system 10 is capable of suggesting one or more configurations for the new order when the user selects item 62. The system 10 uses a compatibility check based on the new order information 42 and the existing infusion map 38 to determine possible ways of connecting the newly ordered drug that are compatible with the existing infusion map, and then suggests one or more of the compatible configurations to the user.

Figure 18:
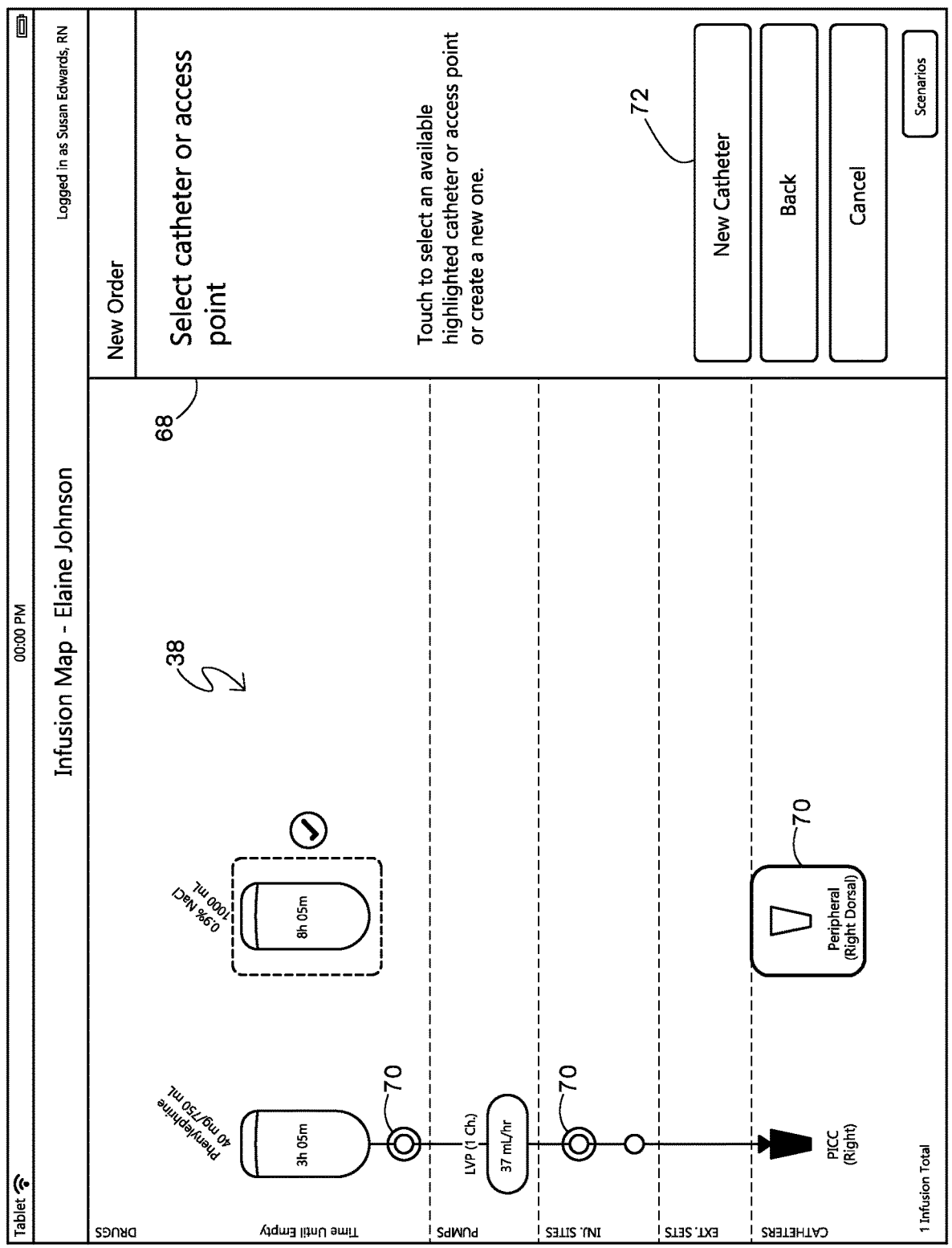
Figure 19:
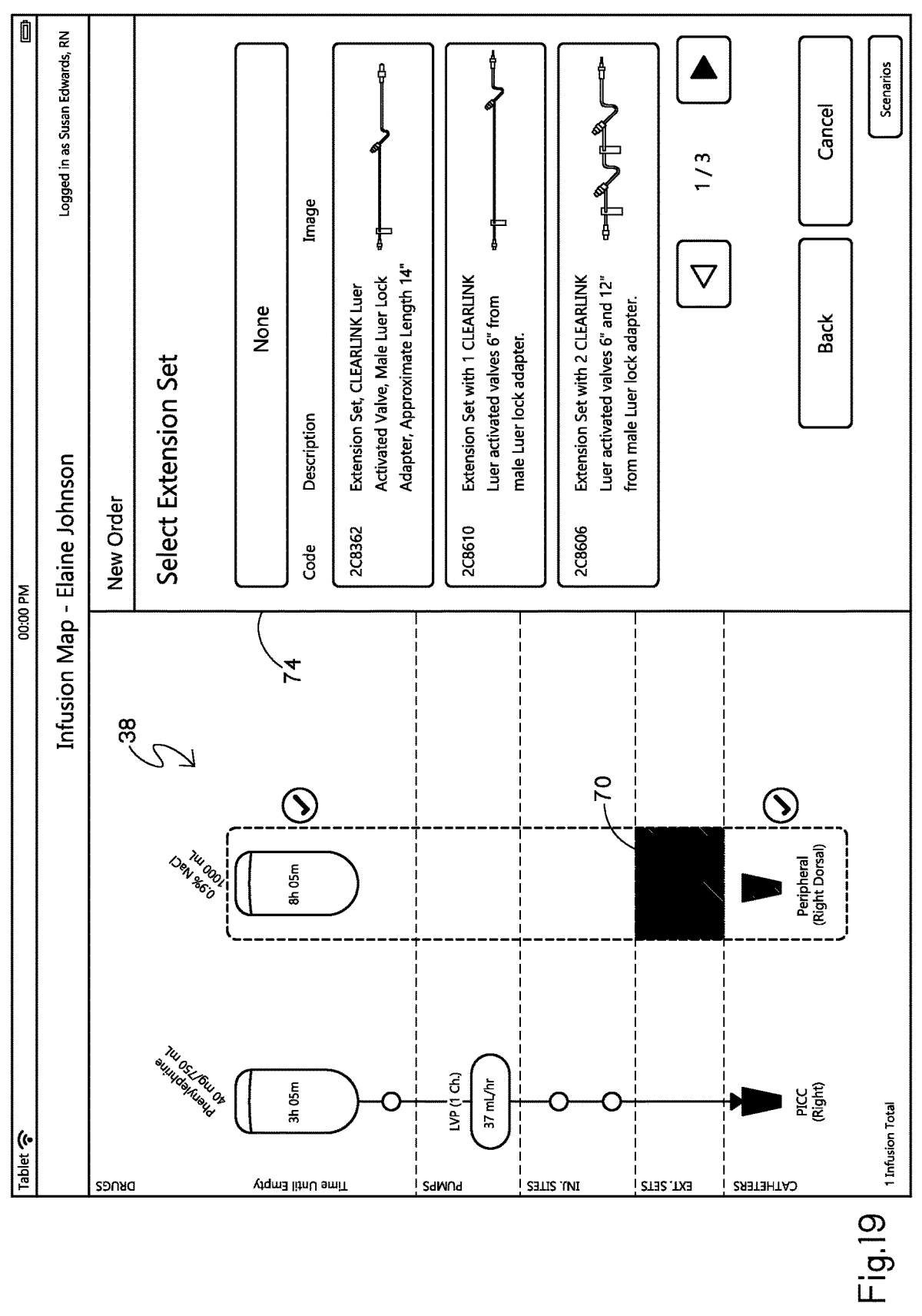
Figure 20:
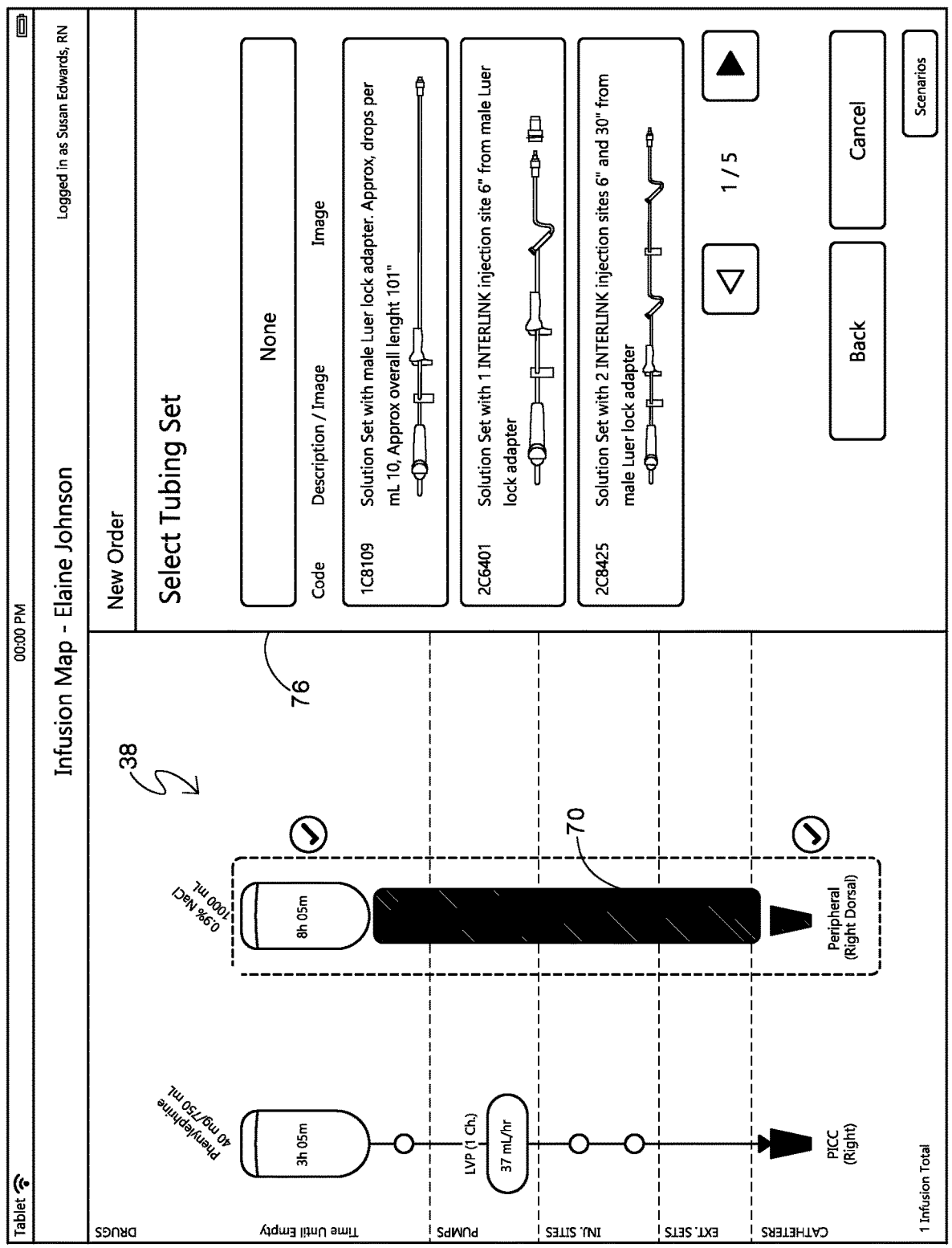
Figure 21:
Figure 22:
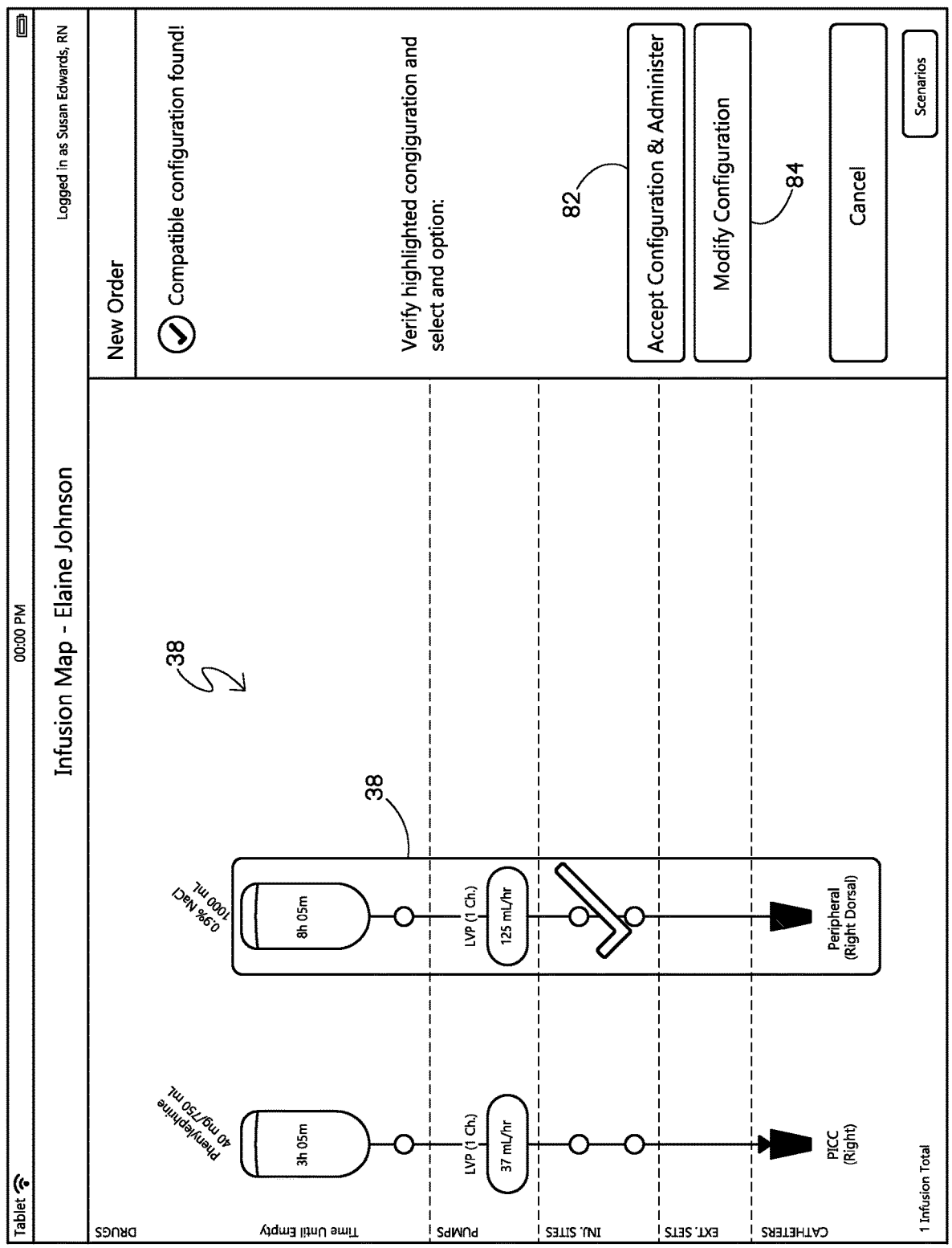
Figure 23:
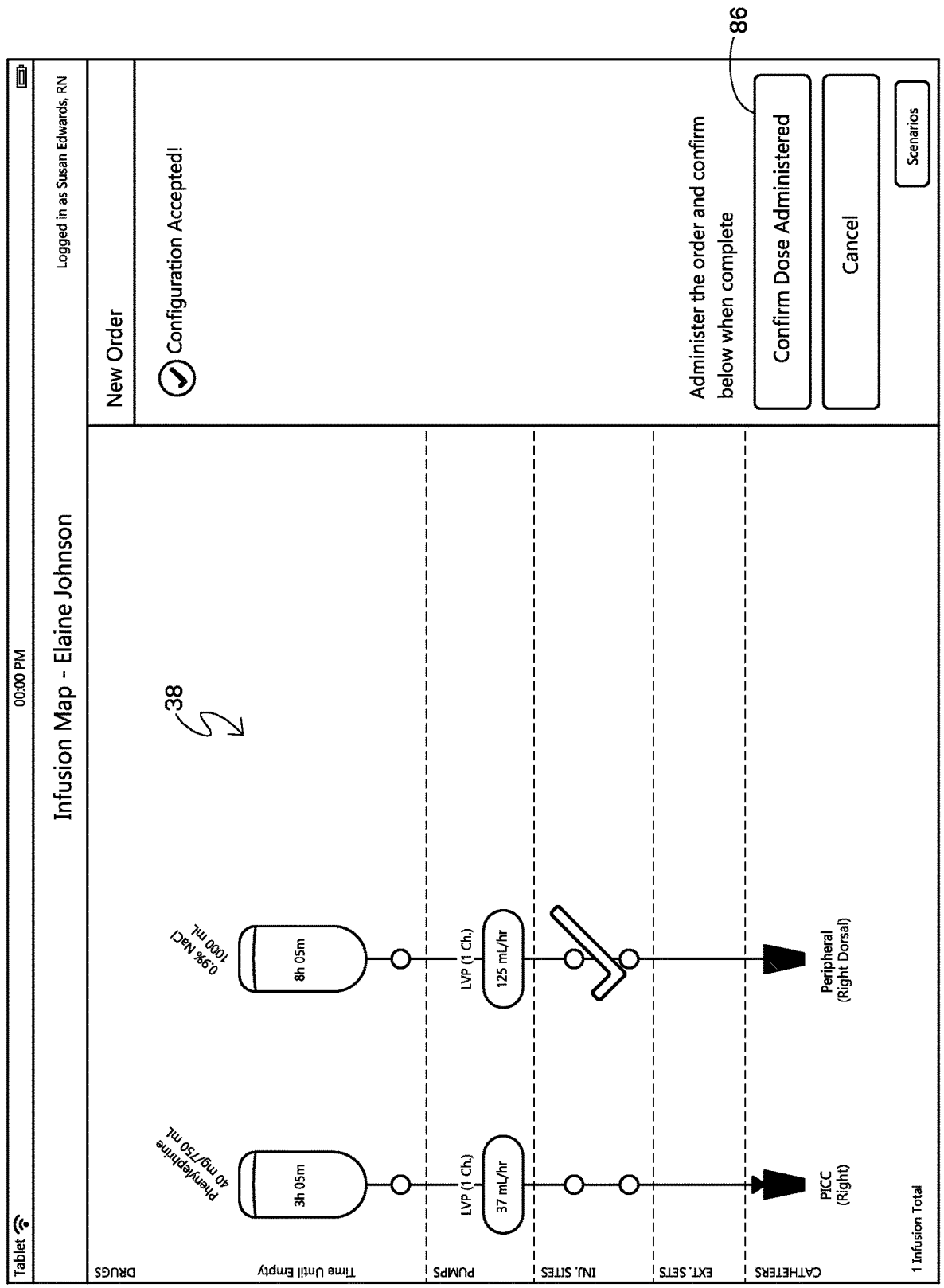
Figure 24:
Figure 25:
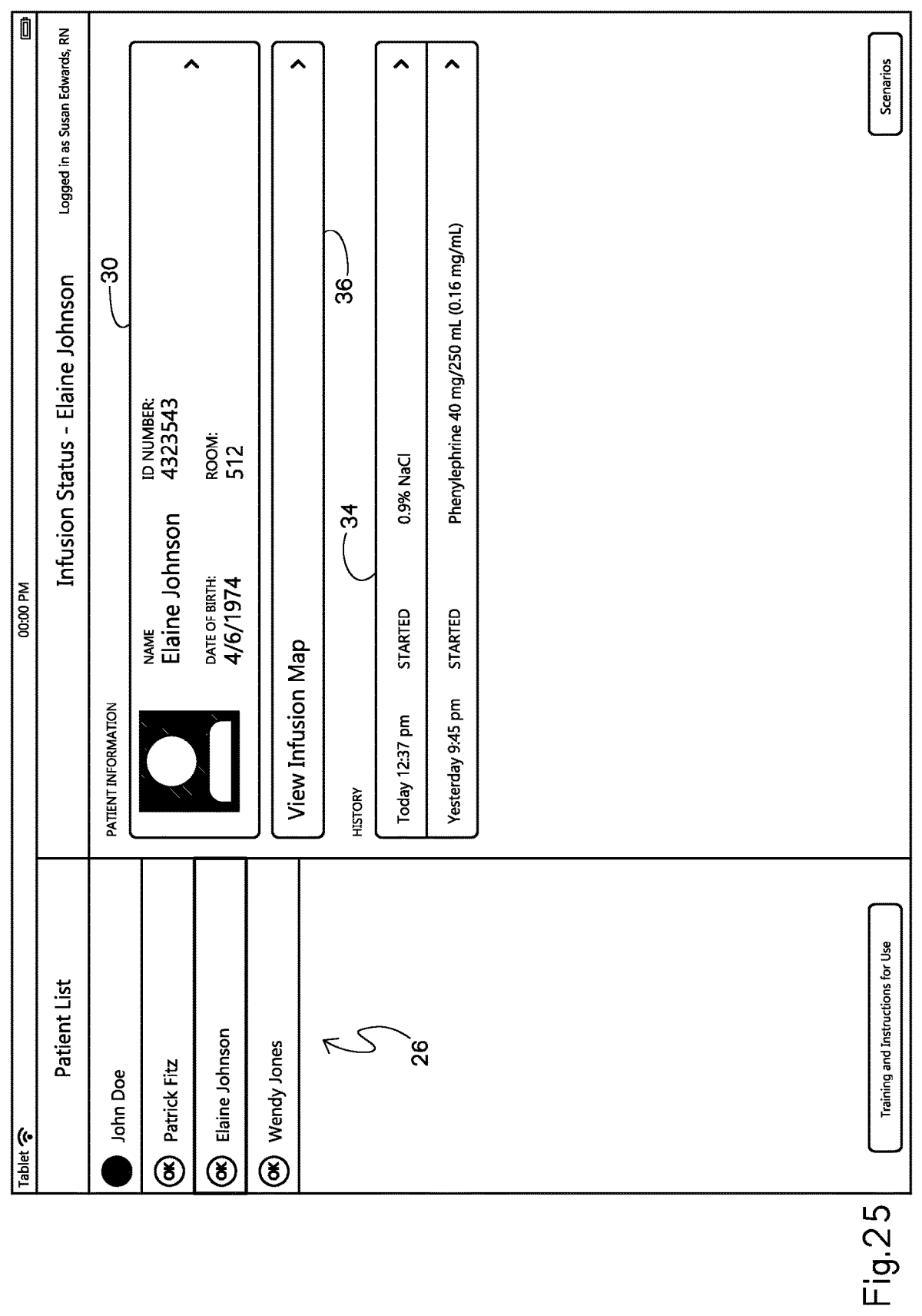
Figure 27:
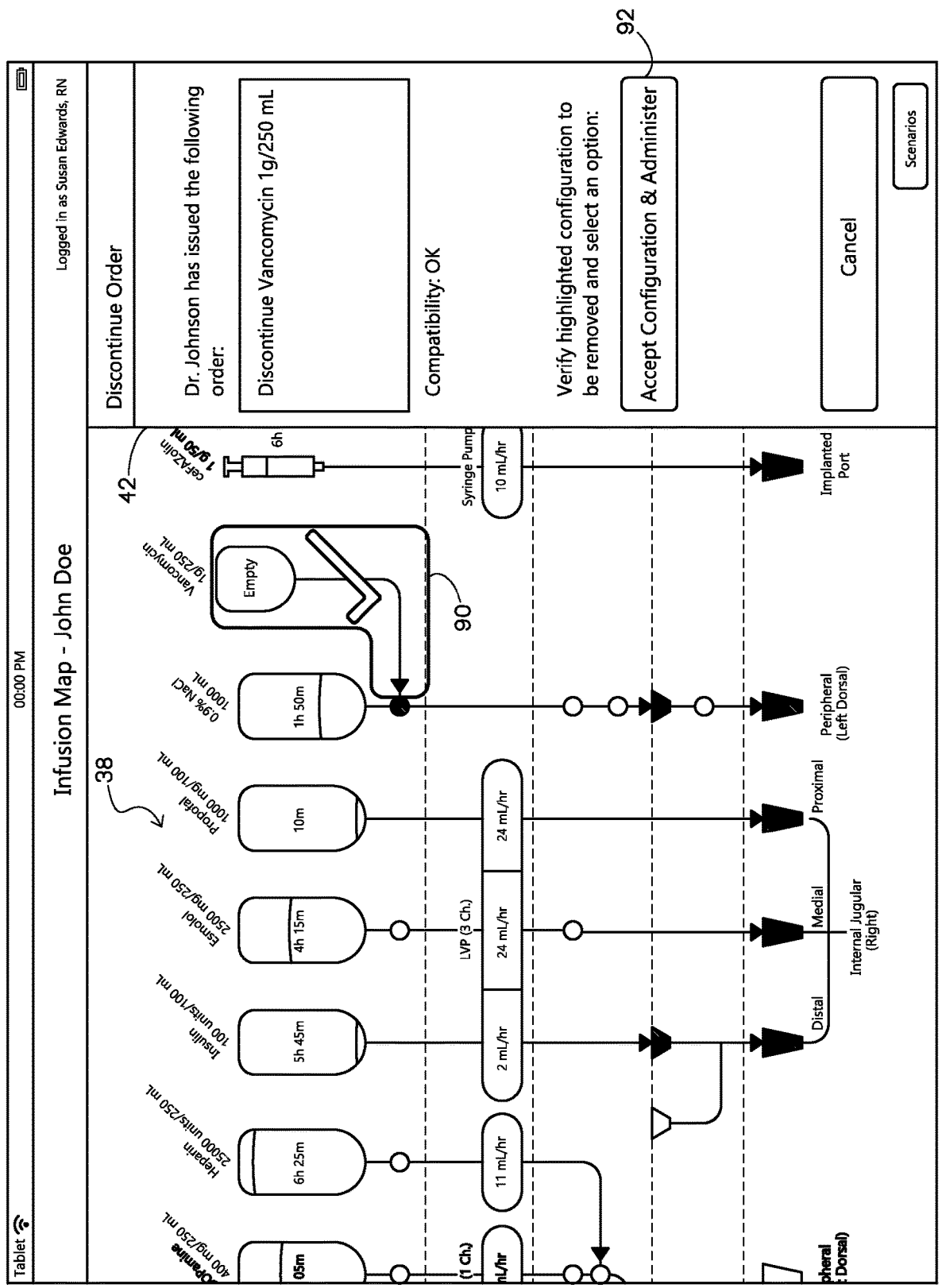

Alternatively, the user may manually configure the setup by selecting item 64. When the user selects a manual configuration, the system 10 first prompts the user to select which catheter or access point the infusion will be connected to at 68. As shown in FIG. 18, candidate access points, including existing catheters and access points, are highlighted 70 on the infusion map 38 to aid the user in selecting a point. Alternatively, the user may select a new catheter 72. Next, as shown in FIG. 19, the user is provided with a list 74 of extension sets for use with the drug. Again, candidate locations 70 are highlighted on the infusion map 38, showing where the extension set can be placed. Similarly, FIG. 20 shows that the user is presented with a list 76 of possible tubing sets and candidate locations 70 within the infusion map 38, and FIG. 21 shows that the user is provided with a list 78 of possible infusion pumps for use with the drug, and highlighted locations 70 where the pump can be positioned. For each of the lists 74, 76, 78, the system 10 provides a list of appropriate equipment options, together with a description and representative image to allow for easy selection by the user. The system 10 preferably displays only the equipment available in a particular hospital or only the equipment available to a particular ward of that hospital. Once the user has selected a configuration for the drug, the system 10 preferably verifies that the configuration is compatible with the existing infusion map 38 using the compatibility checks described above, shows the infusion map 38 with the newly configured portion highlighted 80, and prompts the user to accept the verified configuration 82 or modify the configuration 84, as shown in FIG. 22. The system 10 then displays an updated infusion map 38 and prompts the user to confirm that the dose has been administered 86 as shown in FIG. 23. As shown in FIG. 24, the system confirms that the order has been administered via a confirmation dialog box 88 and updates the patient chart with the time and user administering the order. FIG. 25 shows that the infusion status screen for the patient is updated to include the new order in the history list 34.

Referring now to FIGS. 26-30, the system 10 also allows for orders to be discontinued. A pending action to discontinue an order for patient John Doe is shown in action list 32 on the patient infusion status screen, shown in FIG. 26. When the user selects the pending action, the infusion map 38 is shown, and the system highlights the portion of the map 90 affected by the discontinued order. Additionally, order information 42 is shown indicating the physician who issued the order and order text. In the example shown in FIG. 27, the order text reads "Discontinue Vancomycin 1 g/250 mL." Additionally, as with other orders discussed above, the order information 42 preferably includes compatibility information indicating that the order is compatible with the present infusion map. The user is prompted to accept the new configuration 92 and discontinue administration of the drug as indicated in the order text.

Figure 28:
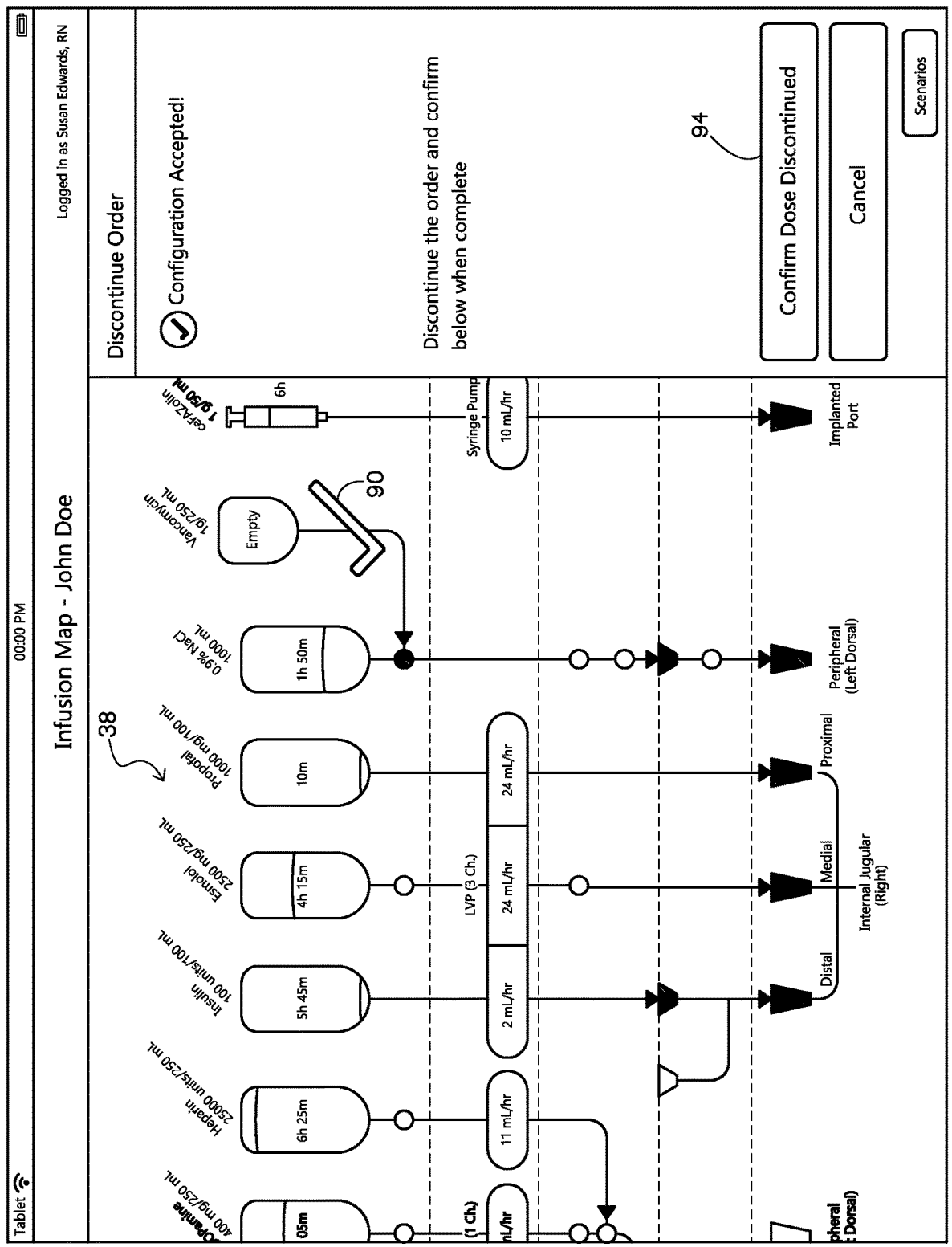
Figure 29:

As shown in FIG. 28, the system 10 then prompts the user to confirm 94 that the dose has been discontinued. Once the user confirms that the dose has been discontinued, the system updates the patient medical record to indicate the time at which the physician order was carried out and the user responsible for carrying out the order, and indicates that the discontinuation order was successfully carried out through a confirmation dialog box 96 presented to the user, as shown in FIG. 29. The patient infusion status screen is updated so that the history list 34 includes the current medical record information, as shown in FIG. 30.

Preferably, each item of hospital equipment and each drug container includes a unique identification code 98 registered in a database accessible by the infusion mapping system 10. Here, an identification code 98 may be any machine-readable representation of data, including visual representations such as traditional parallel-line barcodes, QR codes, or other known systems. Alternatively, the identification code 98 may be stored and read via electronic means, such as RFID tags. As shown in FIGS. 31-42, the system 10 also preferably allows a user to configure a portion of an infusion map 38 based on scanning the one or more identification codes 98 corresponding to the drug container(s) and equipment used to administer the order. Additionally, both the patient and user possess also unique identification codes so that the patient and user can also be identified by the system.

Figure 32:
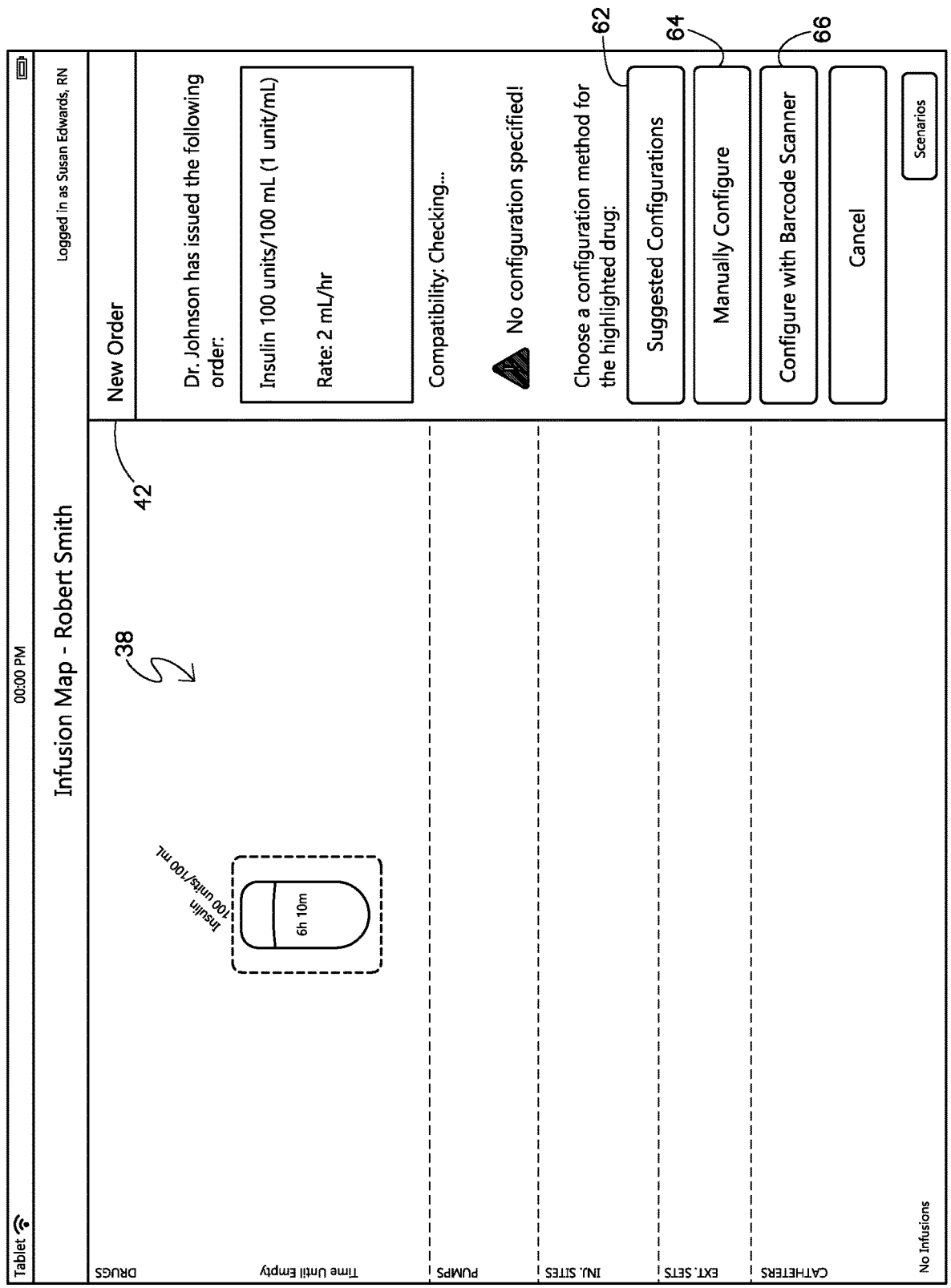
Figure 34:
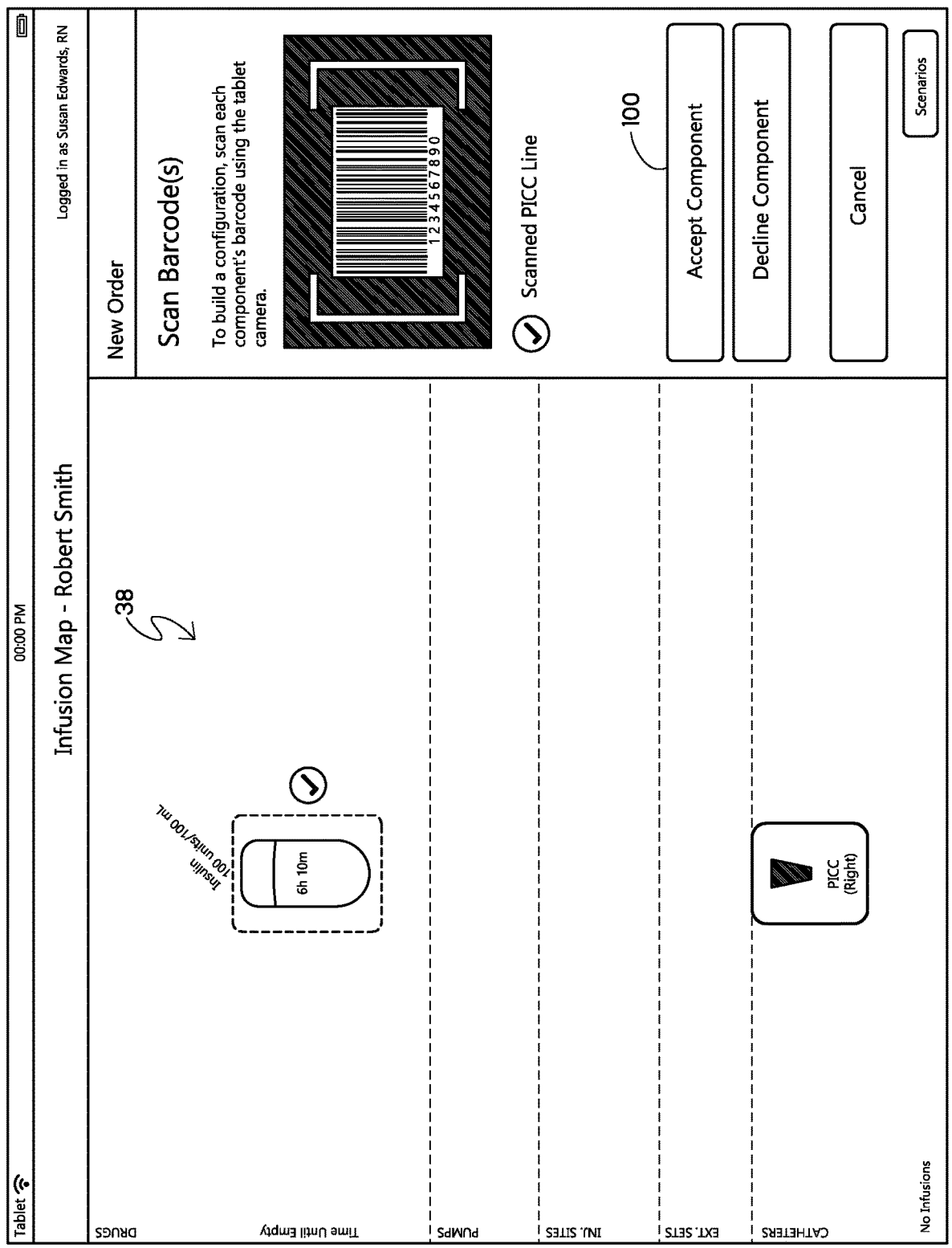
Figure 38:
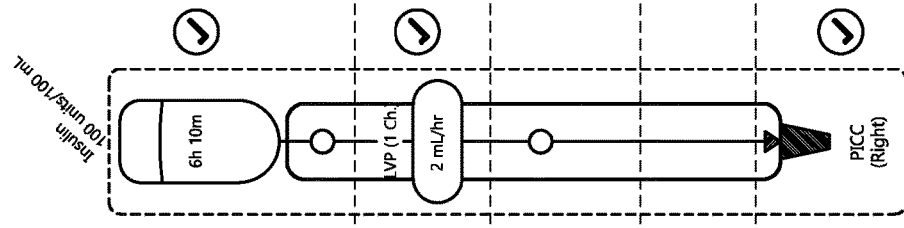
Figure 39:
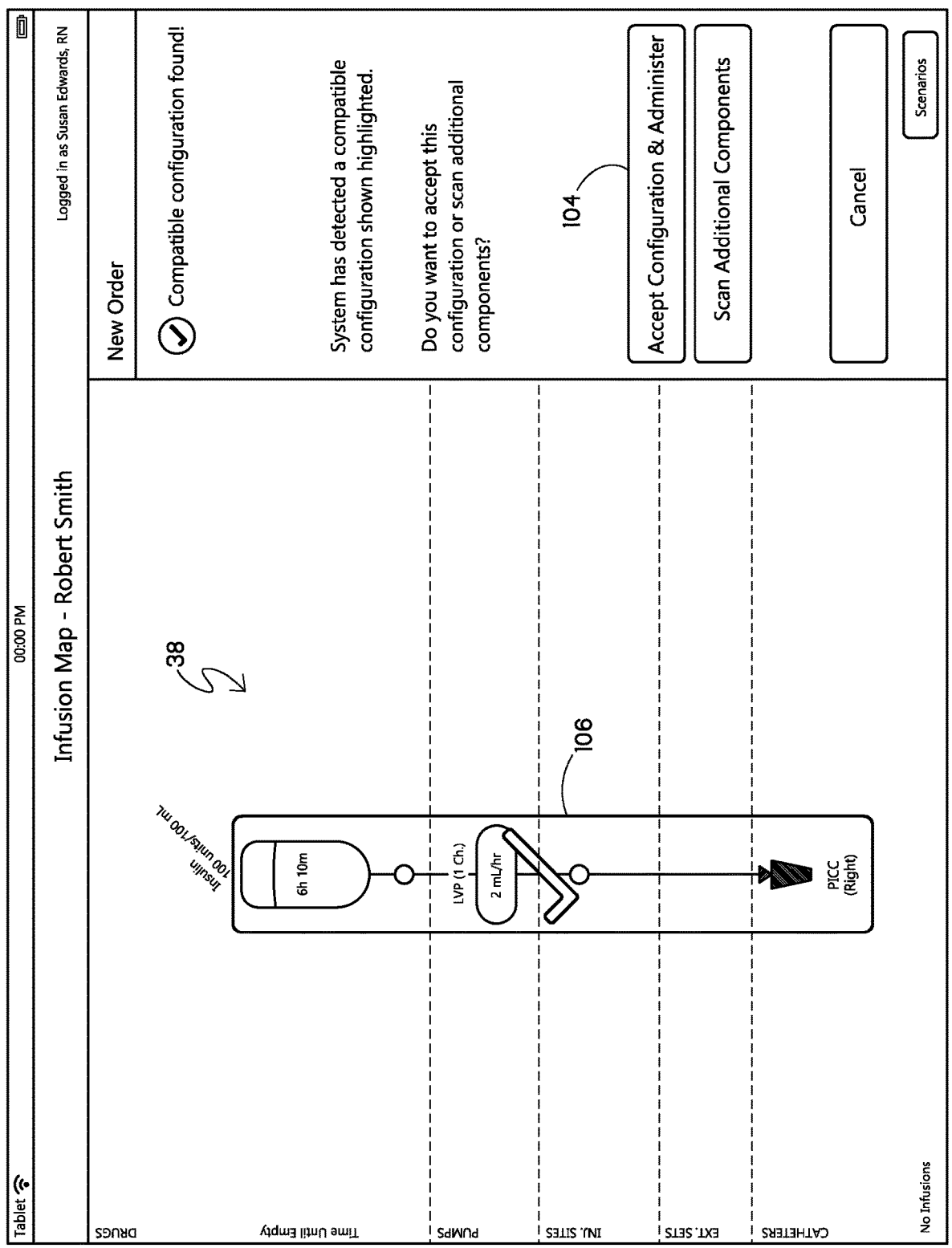
Figure 40:
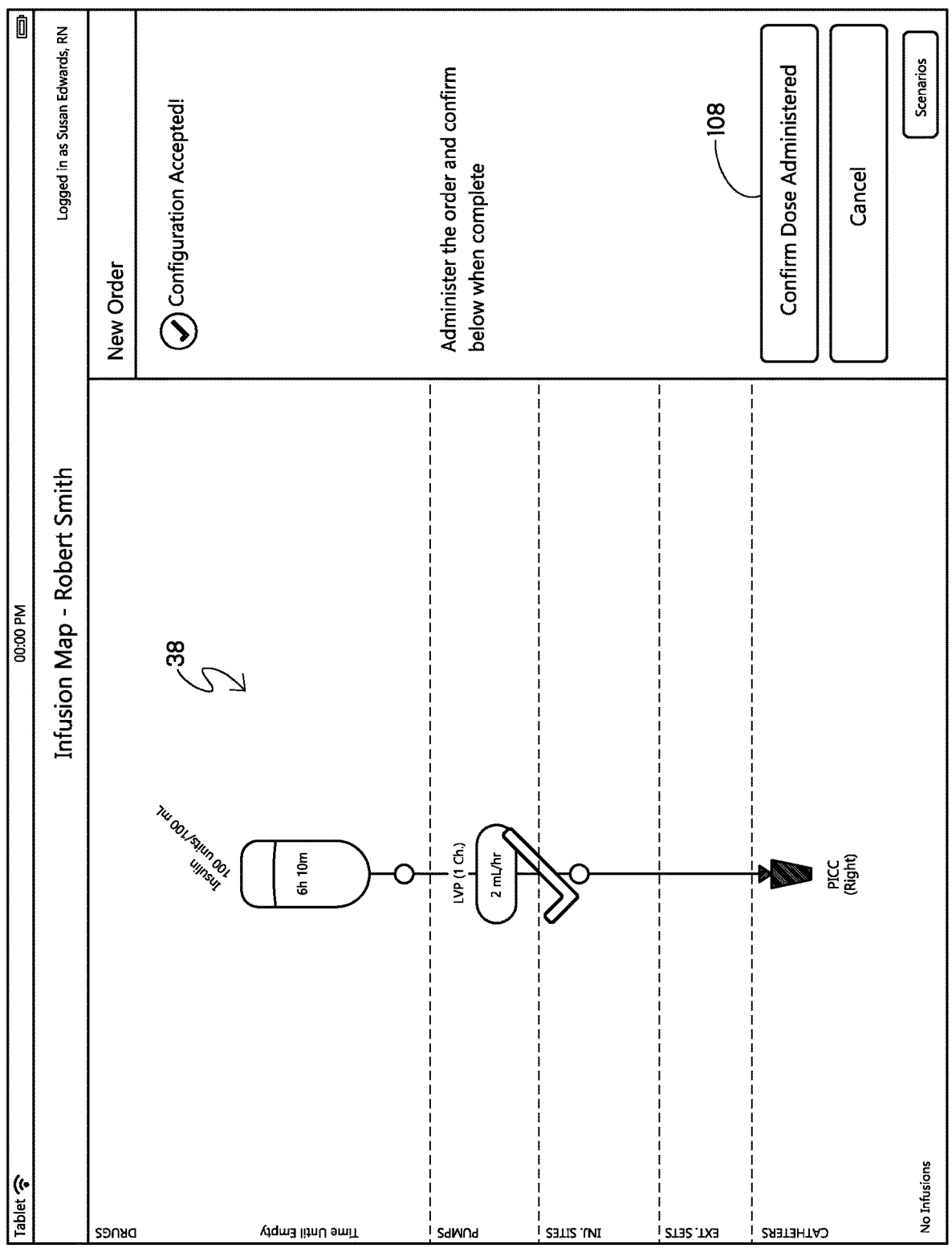
Figure 41:
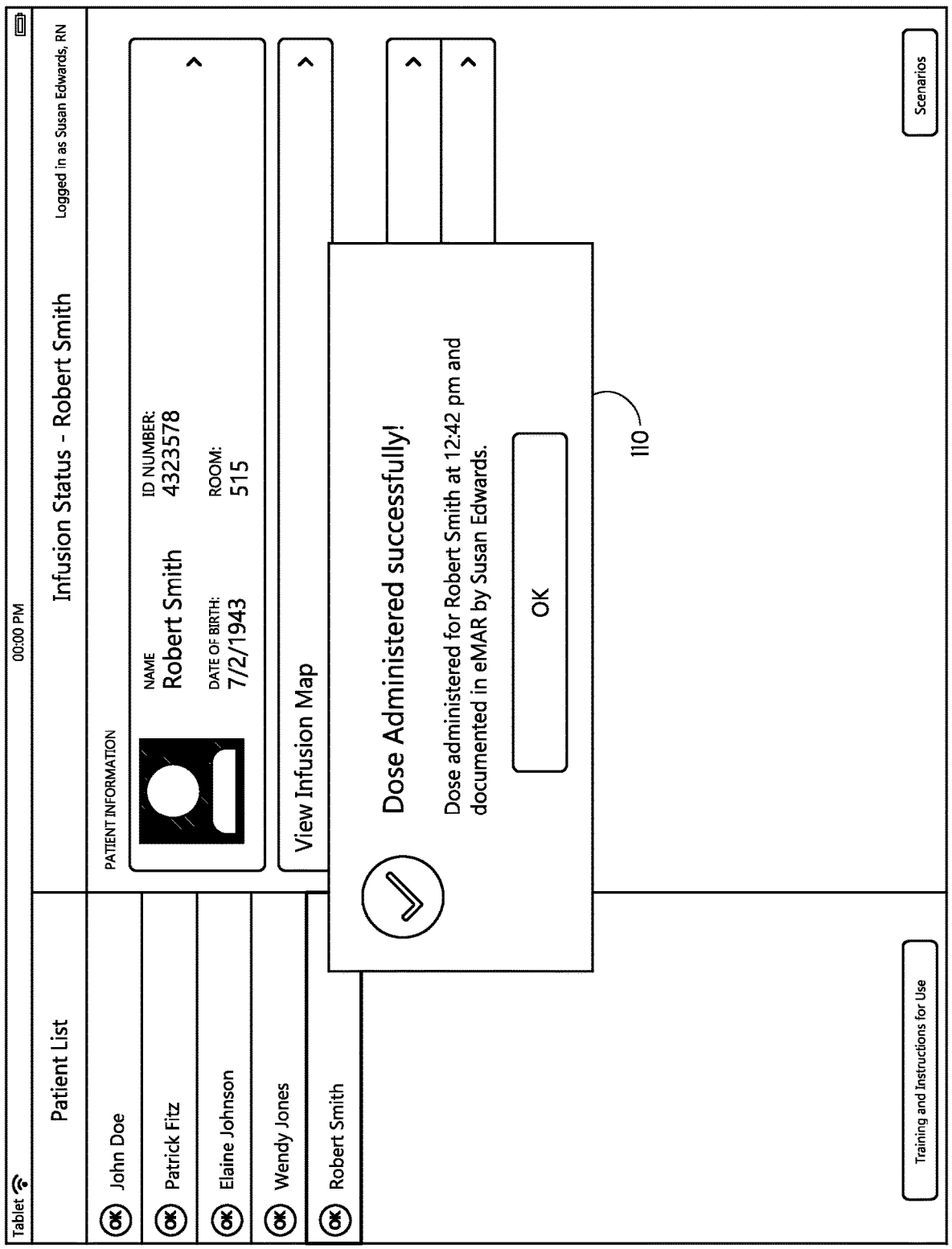

FIG. 31 shows that a pending action for a new order appears in the new order list 32 on the patient infusion status screen. In this case, the patient is a new patient with no existing infusion configuration. As shown in FIG. 32, no configuration is specified for the new order. Accordingly, the system 10 displays order information 32 associated with the new order and prompts the user with several options for configuration, including a suggested configuration 62, including system-suggested configurations and/or a pharmacist- or physician-specified configuration, manual configuration 64 by a nurse using a pick-list selection as described previously, or configuration using a barcode scanner 66. When the user selects "configure with barcode scanner" 66, the system prompts the user to scan barcodes attached to the appropriate hospital equipment using the input device 18, which is preferably any known barcode scanner input device. As non-limiting examples, the input device 18 may be a camera integrated into a laptop computer, personal digital assistant, tablet computer, or smartphone, or a separate scanning device. As each barcode is scanned, the corresponding equipment appears in the infusion map 38, and the system 10 identifies the scanned equipment, prompts the user to verify that the correct equipment has been scanned 100, and prompts the user to scan additional equipment 102, as shown in FIGS. 34-38. While the example illustrated uses barcodes, any known identification code (e.g., QR codes, RFID chips) may be used without departing from the scope of the present invention, as discussed above. Once a complete configuration has been scanned, the system verifies that the configuration is compatible, and prompts the user to accept the configuration 104, while displaying the infusion map 38 with the newly-added equipment highlighted 106, as shown in FIG. 39. The system then prompts the user to confirm that the dose has been administered 108 as shown in FIG. 40. The patient record is updated to include the time that the order was carried out and the user name of the person who administered the order. This information is presented to the user in a confirmation dialog box 110, as shown in FIG. 41. Finally, as shown in FIG. 42, the patient infusion status screen is updated to show that the order was successfully entered into the patient's chart in the history list 34.

Figure 43:
Figure 44:
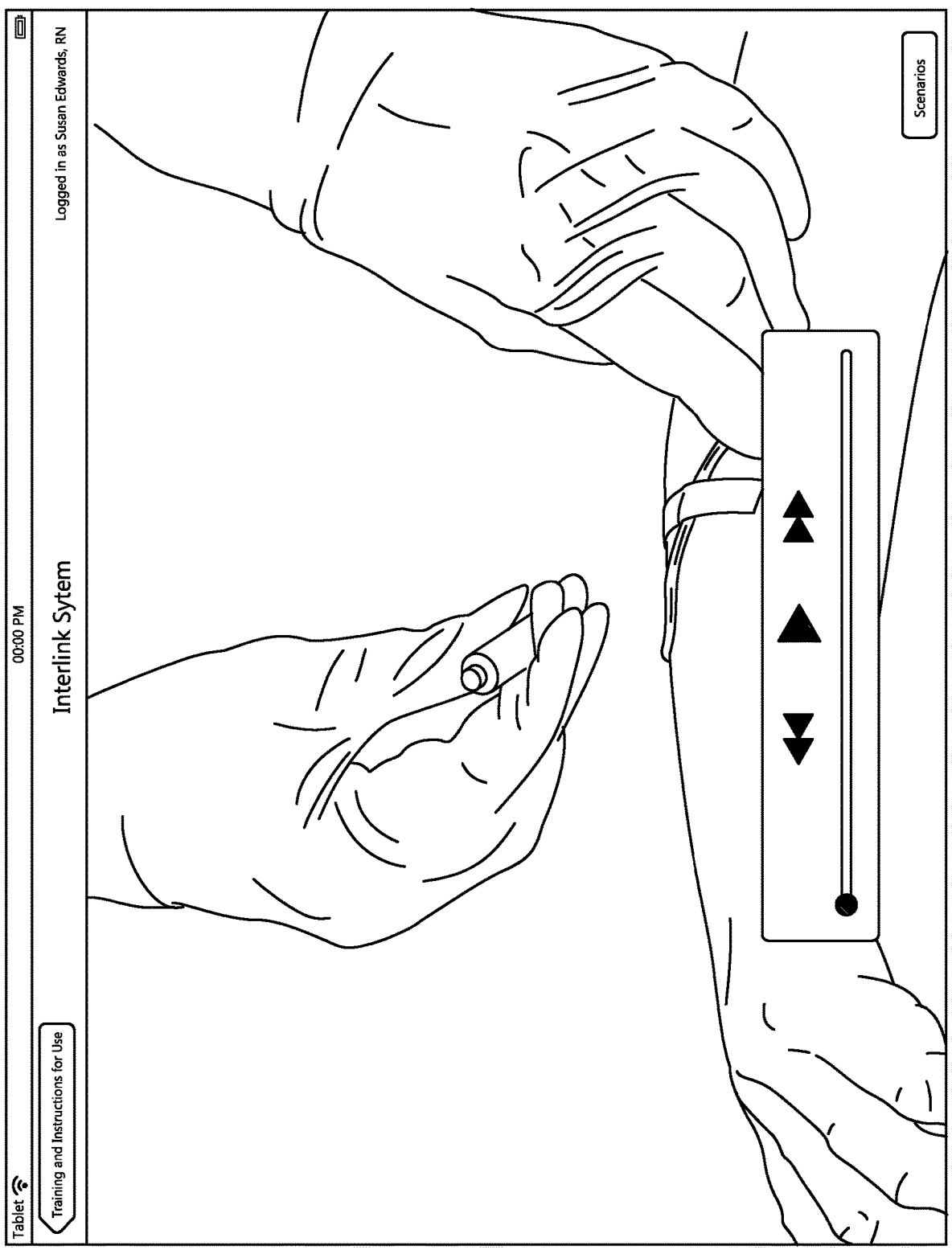
Figure 45:
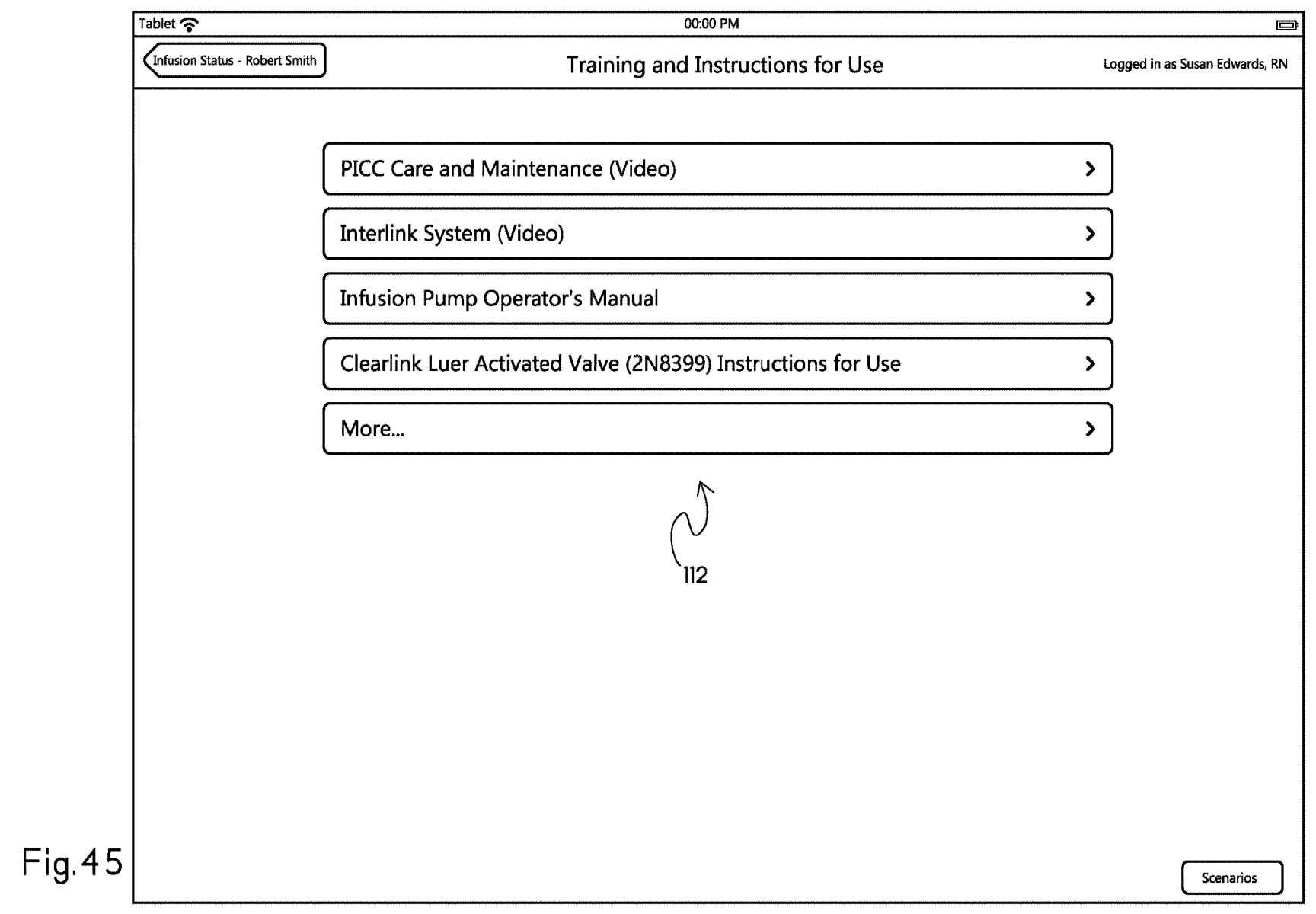
Figure 46:
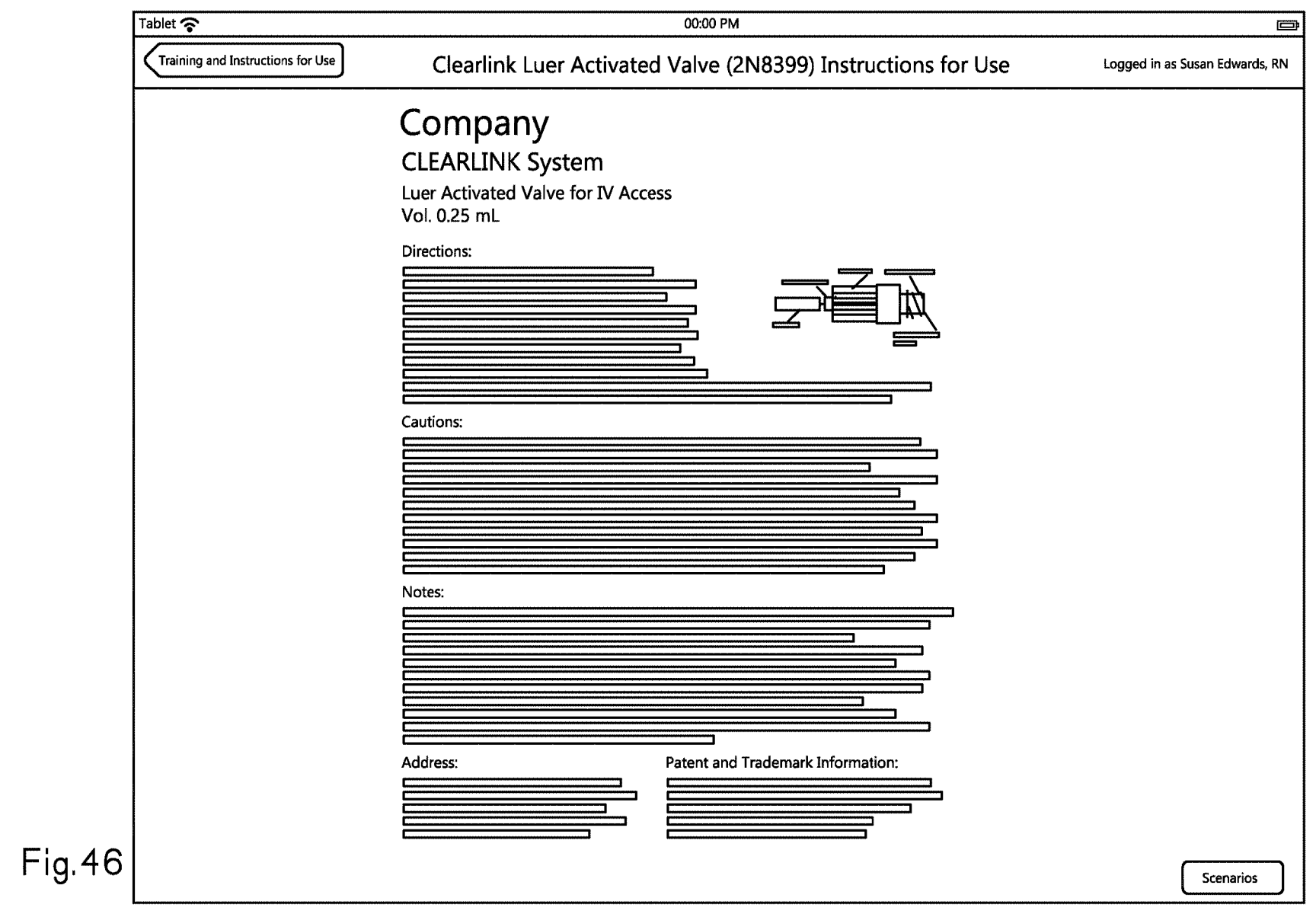

As shown in FIGS. 43-46, the system also provides training and instruction for use information related to the equipment used to administer intravenous drugs. Preferably, multiple training and instruction items are available in a plurality of formats, including, for example, videos, instruction manuals, and the like. The items may be stored locally on the user's device (e.g., in the memory of a user's tablet, smartphone, etc.), centrally on a server accessible by all system devices (e.g., a hospital data server), or remotely, such that the training and instruction items are available via the Internet. As shown in FIG. 43, the system 10 provides the user with a menu 112 showing a selection of training and instructional use content. In response to a user selecting an item of video content, the system retrieves the selected video via a known method (e.g., playback from memory, progressive download, streaming, etc.) and begins playback, as shown in FIG. 44. When the video finishes, or in response to a user interaction, the system returns to the training and instruction menu, as shown in FIG. 45. FIG. 46 shows an example of a text-based instruction item. Text based items may be, for example scanned documentation provided by the equipment manufacturer, and are preferably searchable documents.

Additionally, the infusion map system 10 optionally includes more advanced medical record functionality, including notation of non-intravenously administered drugs, notation of laboratory test orders and test results, and additional physician orders and actions taken. The system 10 further optionally includes more advanced patient charting features.

Further, the system 10 is optionally integrated with other medical information systems present at the medical facility including, but not limited to, inventory management systems and billing systems. This integration advantageously increases accuracy of inventory and billing, while simultaneously reducing duplicative work of noting drugs provided for inventory and billing purposes by hospital staff and health care providers.

Still further, the system optionally includes "personal nursing assistant" (PNA) functionality, planning a nursing schedule based on assigned patients and patient orders. This desirably ensures that nurses are provided with a manageable schedule that allows them adequate time to see to patient needs, while also reducing scheduling time for hospital administration. This functionality preferably includes smart triage functionality, arranging orders for a nurse according to multiple factors such as patient condition, medication criticality, and other competing orders.

The system 10 also may be integrated with patient monitoring and notification systems. This integration provides the user with a triage action item when a notification such as an equipment alarm is received.

While at least one exemplary embodiment has been presented in the foregoing detailed description in connection with specific apparatus and applications, it should be appreciated that a vast number of variations exist. It should also be appreciated that the exemplary embodiment is merely an example, and is not intended to limit the scope, applicability, or configuration in any way. Rather, the foregoing detailed description will provide those of skill in the art with a convenient road map for implementing an exemplary embodiment of the invention. It will be understood that various changes may be made in the function and arrangement of elements described in an exemplary embodiment without departing from the scope of the invention as set forth in the appended claims.

The invention claimed is:

1. A patient information system comprising:
a memory storing at least one infusion mapping instruction;
a processor that executes the at least one infusion mapping instruction;
a display device that, using the processor, displays at least a portion of an electronic medical record associated with a patient, and graphically transforms the electronic medical record into an infusion map interactively illustrating associated infusion system components in relation to an infusion therapy;
a diagramming unit that, using the processor, receives the electronic medical record and generates the infusion map showing all intravenous drugs being administered to the patient, wherein, for each of the drugs, the infusion map further illustrating a route of administration for the drug;
a building unit that, using the processor, builds a virtual infusion configuration of an infusion device arrangement, including at least one option for a plurality of infusion equipment associated with the infusion therapy, using the display device by interactively establishing virtual links between the drug and the associated infusion system components in relation to the infusion therapy, each virtual link graphically representing a visual connection between the associated infusion system components, the virtual links comprising at least an interactive representative image of the intravenous drug and an interactive representative image of the route of administration for the intravenous drug, wherein said infusion map schematically represents a list of drugs being administered to the patient intravenously as interactive representative images and, for each of the drugs being administered, schematically represents at least a catheter port at which the drug is entering the patient's body as an interactive representative image and an indication of tubing connecting the drug to the catheter port as an interactive representative image;
an order administering unit that, using the processor, receives order information for an ordered drug displays at least a portion of the infusion map with a recommended configuration for administration of the ordered drug including the ordered drug and at least one associated infusion system component as interactive representative images, highlights at least a portion of the displayed recommended configuration, and in response to receiving an acceptance of the recommended configuration, alters the infusion map to include the recommended configuration; and
a record updating unit that, using the processor, automatically updates the electronic medical record to correspond to the altered infusion map, and automatically records a history of the updated electronic medical record in the memory based on the altered infusion map.

2. The patient information system of claim 1, wherein said order administration unit further comprises:
determining compatibility of the new order with the infusion map; and
updating the infusion map as specified in the new order.

3. The patient information system of claim 2, wherein said determining compatibility comprises:
comparing the received order information with patient allergy information stored in the electronic medical record associated with the patient;
determining whether there are any physical incompatibilities between the received order information and the infusion map; and
checking for mass flow balance errors in the received order information.

4. The patient information system of claim 1, wherein said updating comprises automatically generating one or more changes to the infusion map based on the received order information.

5. The patient information system of claim 1, wherein said updating comprises:
generating a list of one or more configurations for use with the new order information;
presenting said list of one or more components to a user including the highlighted recommended configuration;

receiving a user selection from among said one or more listed components; and updating said infusion map to include said selected component.

6. The patient information system of claim 1, wherein said updating comprises:

receiving bar code information from a code reader;

comparing said received bar code information with an equipment database to determine which piece of said infusion equipment was scanned; and updating said infusion map to include said scanned infusion equipment.

7. A computer-implemented infusion mapping process comprising:

storing at least one infusion mapping instruction in a memory;

executing the at least one infusion mapping instruction stored in the memory using a processor;

retrieving and displaying, using the processor, at least a portion of an electronic medical record associated with a patient on a display device;

graphically transforming, using the processor, the electronic medical record into an infusion map by interactively illustrating associated infusion system components on the display device in relation to an infusion therapy;

generating the infusion map, using the display device and the processor, by schematically showing all intravenous drugs being administered to the patient based on the retrieved electronic medical record, wherein for each of the drugs the schematic diagram illustrates a route of administration for the drug;

building, using the processor, a virtual infusion configuration of an infusion device arrangement, including at least one option for a plurality of infusion equipment associated with the infusion therapy, using the display device by interactively establishing virtual links between the drug and the associated infusion system components in relation to the infusion therapy, each virtual link graphically representing a visual connection between the associated infusion system components, the virtual links comprising at least an interactive representative image of the intravenous drug and an interactive representative image of the route of administration for the intravenous drug, wherein said infusion map schematically represents a list of drugs being administered to the patient intravenously as interactive representative images and, for each of the drugs being administered, schematically represents at least a catheter port at which the drug is entering the patient's body as an interactive representative image and an indication of tubing connecting the drug to the catheter port as an interactive representative image;

receiving new order information, using the processor, for an ordered drug displaying at least a portion of the infusion map with a recommended configuration for administration of the ordered drug including the ordered drug and at least one associated infusion system component as interactive representative images, highlighting at least a portion of the displayed recommended configuration, and in response to receiving an acceptance of the recommended configuration, altering the infusion map to include the recommended configuration; and automatically updating, using the processor, said electronic medical record to correspond to the altered infusion map, and automatically recording a history of the updated electronic medical record based on the altered infusion map.

8. The infusion mapping process of claim 7, further comprising checking compatibility of said received new order information with said infusion map, wherein said update is performed when there is no compatibility problem between said received new order information and said infusion map.

9. The infusion mapping process of claim 7, wherein, for each of the drugs being administered, said infusion map stores information regarding at least a catheter port at which the drug is entering the patient's body and said associated infusion equipment connecting the drug to the catheter port.

10. The infusion mapping process of claim 7, wherein said new order includes new order information specifying a drug to be administered to the patient and said infusion equipment for connecting the drug to the patient, and wherein said updating comprises adding said infusion equipment to the infusion map based on said received new order information.

11. The infusion mapping process of claim 7, wherein said updating comprises:

maintaining a database storing a plurality of pieces of said infusion equipment and, for each said piece of said infusion equipment, associating an identifying code therewith;

receiving, as input data from a code reader;

comparing the received data with said plurality of identifying codes stored in said database;

selecting a piece of said infusion equipment on the basis of said received data matching said identifying code associated therewith; and adding said selected piece of said infusion equipment to said infusion map.

12. A hospital information system comprising:

a memory storing at least one infusion mapping instruction;

a processor that executes the at least one infusion mapping instruction;

a display device that, using the processor, displays at least a portion of the plurality of patient electronic medical records associated with a patient, and graphically transforms the plurality of patient electronic medical records into an infusion map interactively illustrating associated infusion system components in relation to an infusion therapy;

an infusion mapping device which, using the processor, performs operations including:

retrieving at least a portion of one or more patient electronic medical records, including a portion specifying intravenous drugs being administered to the patient and infusion equipment associated with the administration of the drugs;

for each of said one or more retrieved medical records, displaying the infusion map that schematically represents said portion specifying intravenous drugs being administered and the associated infusion system components;

building a virtual infusion configuration of an infusion device arrangement, including at least one option for a plurality of said infusion equipment associated with the infusion therapy, using the display device by interactively establishing virtual links between the drug and the associated infusion system components in relation to the infusion therapy, each virtual link graphically representing a visual connection between the associated infusion system components, the virtual links comprising at least an interactive representative image of the intravenous drug and an interactive representative image of the route of administration for the intravenous drug, wherein said infusion map schematically represents a list of drugs being administered to the patient intravenously as interactive representative images and, for each of the drugs being administered, schematically represents at least a catheter port at which the drug is entering the patient's body as an interactive representative image and an indication of tubing connecting the drug to the catheter port as an interactive representative image;

modifying said infusion map having the drug and the associated infusion system components;

automatically updating said electronic medical record based on said modified infusion map; and automatically saving said updated electronic medical record based on said modified infusion map.

13. The hospital information system of claim 12, wherein said electronic medical records are stored on an electronic medical record server,
   wherein access to each of said patient electronic medical records stored on said electronic medical record server is permitted for a particular set of one or more user names,
   wherein infusion mapping further performs operations of receiving at least a user name and password, and
   wherein said retrieving retrieves only those medical records which the received username is permitted to access.

14. The hospital information system of claim 13, wherein said infusion mapping device communicates with said electronic medical record server using a wireless communication interface.

* * * * *